US008118805B2

(12) United States Patent
Jinno et al.

(10) Patent No.: US 8,118,805 B2
(45) Date of Patent: Feb. 21, 2012

(54) ROBOT AND MANIPULATOR

(75) Inventors: Makoto Jinno, Tokyo (JP); Takamitsu Sunaoshi, Yamato (JP); Shiro Tsukada, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1484 days.

(21) Appl. No.: 11/511,338

(22) Filed: Aug. 29, 2006

(65) Prior Publication Data

US 2007/0049435 A1   Mar. 1, 2007

(30) Foreign Application Priority Data

Aug. 30, 2005  (JP) ................................ 2005-250076

(51) Int. Cl.
*A61B 17/00* (2006.01)
(52) U.S. Cl. ................................. 606/1; 901/36; 901/49
(58) Field of Classification Search ........ 606/1; 244/230; 901/2, 11, 21, 25, 49; 600/102, 104–108
See application file for complete search history.

(56) References Cited

U.S. PATENT DOCUMENTS

| | | | | |
|---|---|---|---|---|
| 3,243,148 A | * | 3/1966 | Morris et al. | 244/230 |
| 3,717,231 A | * | 2/1973 | Kaufelot | 901/49 |
| 3,935,754 A | * | 2/1976 | Comollo | 244/213 |
| 4,344,729 A | * | 8/1982 | Orsinger et al. | 901/49 |
| 4,702,668 A | * | 10/1987 | Carlisle et al. | 901/25 |
| 4,848,546 A | * | 7/1989 | McCormick et al. | 901/49 |
| 5,529,159 A | * | 6/1996 | Troccaz | 901/25 |
| 5,650,704 A | | 7/1997 | Pratt et al. | |
| 5,797,900 A | | 8/1998 | Madhani et al. | |
| 6,213,906 B1 | * | 4/2001 | Codatto | 901/25 |
| 6,699,177 B1 | * | 3/2004 | Laby et al. | 600/102 |
| 6,889,116 B2 | | 5/2005 | Jinno | |
| 6,994,716 B2 | | 2/2006 | Jinno et al. | |
| 7,043,338 B2 | | 5/2006 | Jinno | |
| 2004/0199147 A1 | | 10/2004 | Nishizawa et al. | |
| 2004/0266574 A1 | | 12/2004 | Jinno et al. | |
| 2005/0222587 A1 | | 10/2005 | Jinno et al. | |

FOREIGN PATENT DOCUMENTS

| | | |
|---|---|---|
| JP | 62-25189 | 2/1987 |
| JP | 3-178795 | 8/1991 |
| JP | 8-229750 | 9/1996 |
| JP | 10-34585 | 2/1998 |
| JP | 11-070488 | 3/1999 |
| JP | 2000-350735 | 12/2000 |
| JP | 2002-102248 | 4/2002 |
| JP | 2002-263116 | 9/2002 |
| JP | 2004-301275 | 10/2004 |
| JP | 2004-321492 | 11/2004 |
| WO | WO 2005/046500 A1 | 5/2005 |

OTHER PUBLICATIONS

Kouichi Watabe, et al., "Development of Link Driven Multi DOF Active Forceps", 2001 JSMZ Conference on Robotics and Mechatronics, 2001, pp. 2P1-D10(1)-2P1-D10(2), with English Abstract.

* cited by examiner

*Primary Examiner* — David Shay
(74) *Attorney, Agent, or Firm* — Oblon, Spivak, McClelland, Maier & Neustadt, L.L.P.

(57) ABSTRACT

A robot has a flexible power transmission member, an input rotation axis rotated by a power generation source, a driving link connected at both ends of the flexible power transmission member, which transmits a rotation torque of the input rotation axis to the flexible power transmission member, and a driven pulley around which the flexible power transmission member is hung.

9 Claims, 20 Drawing Sheets

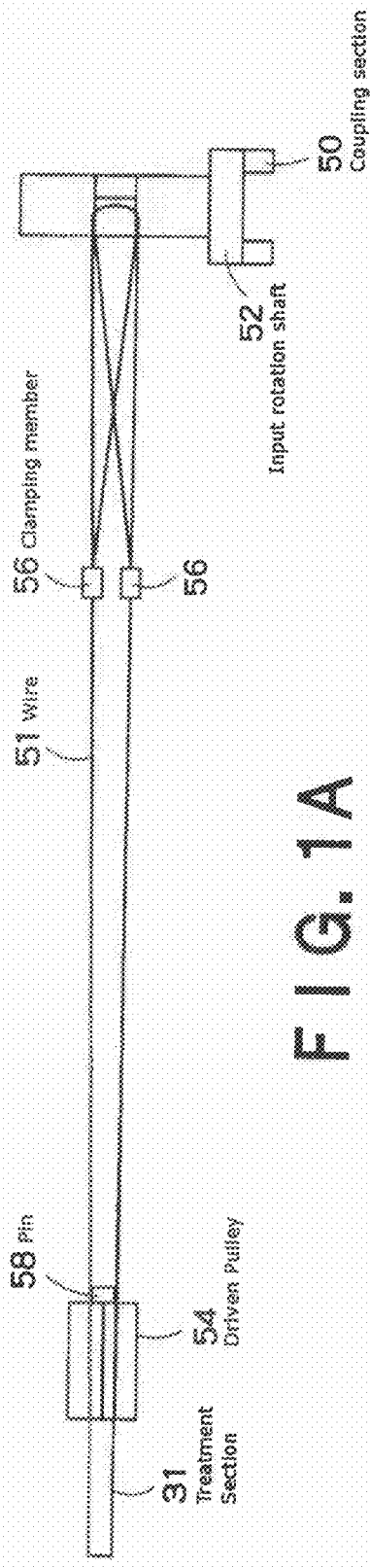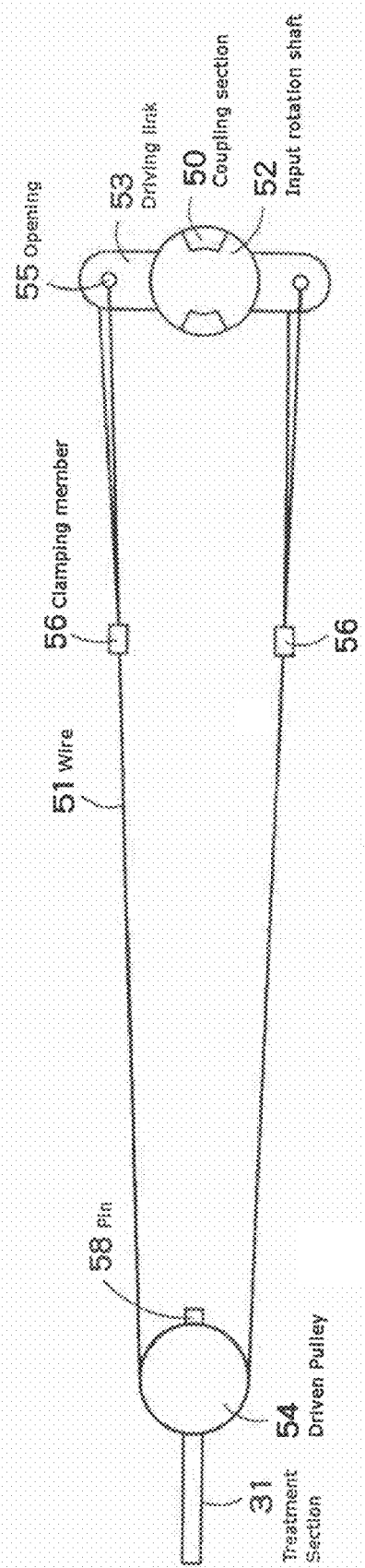

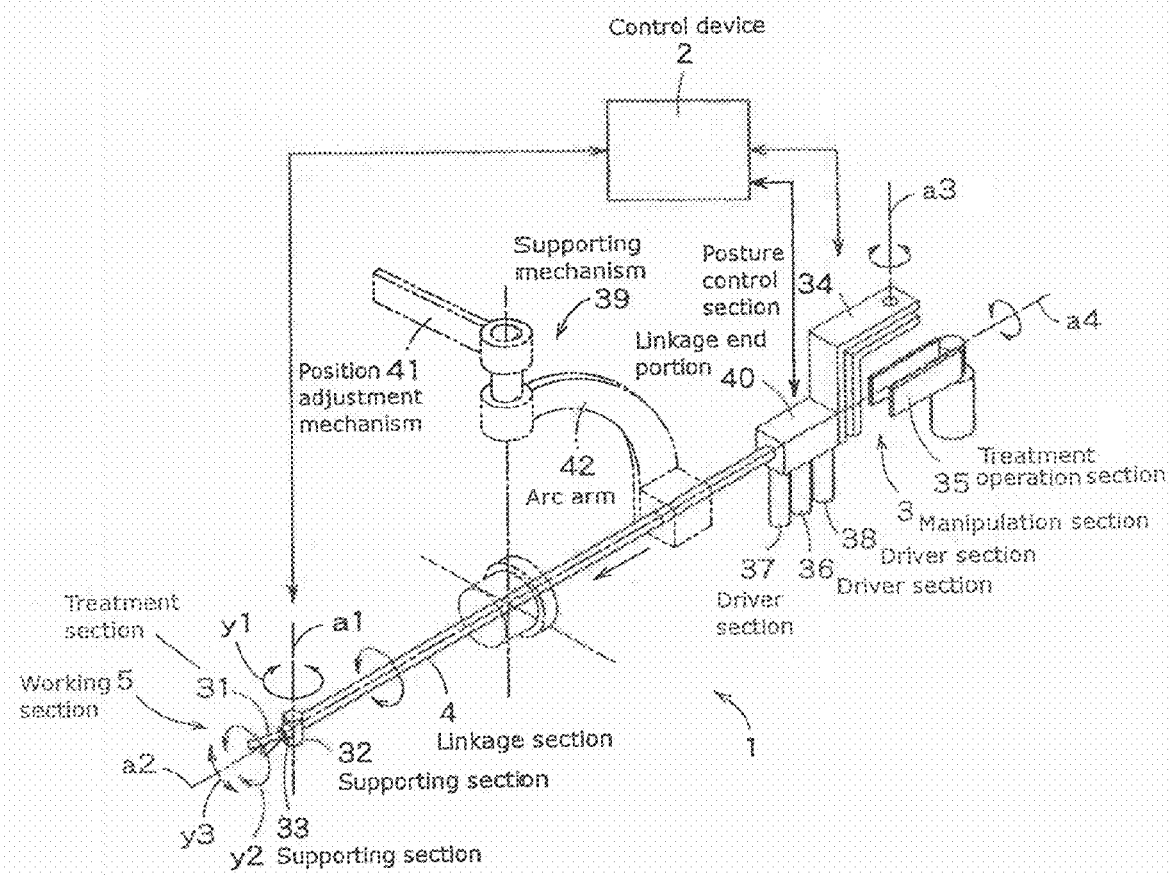
F I G. 5

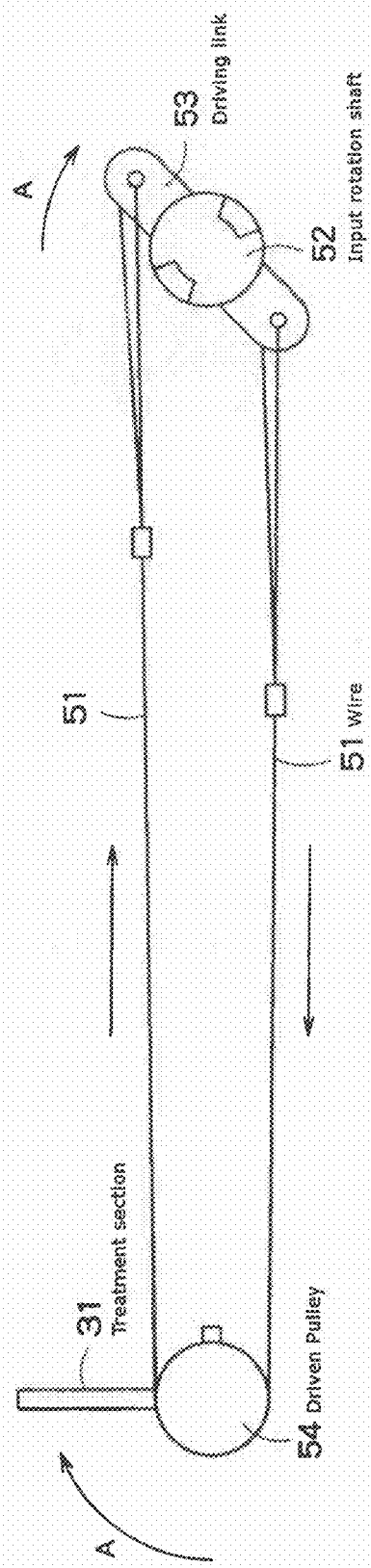
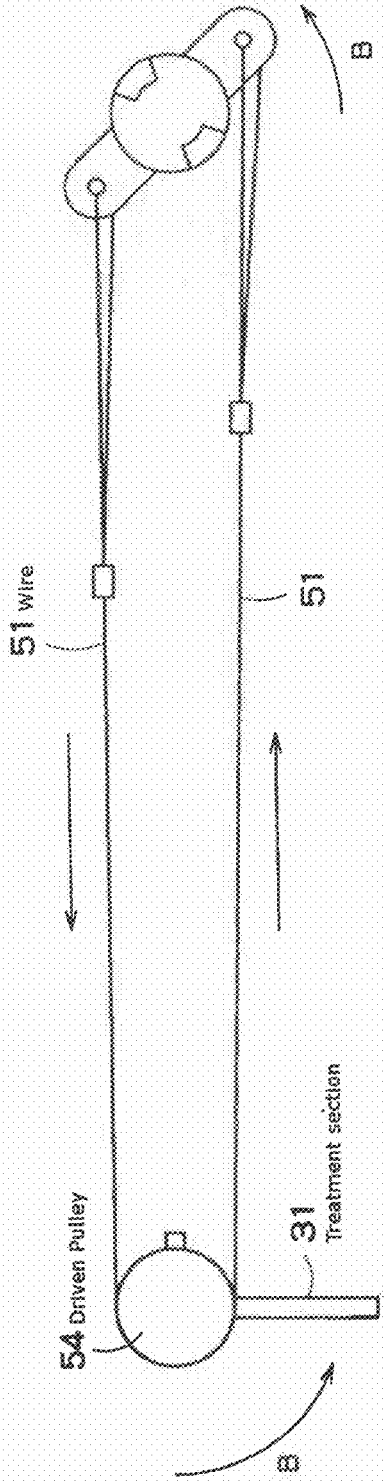
F I G. 8A  F I G. 8B

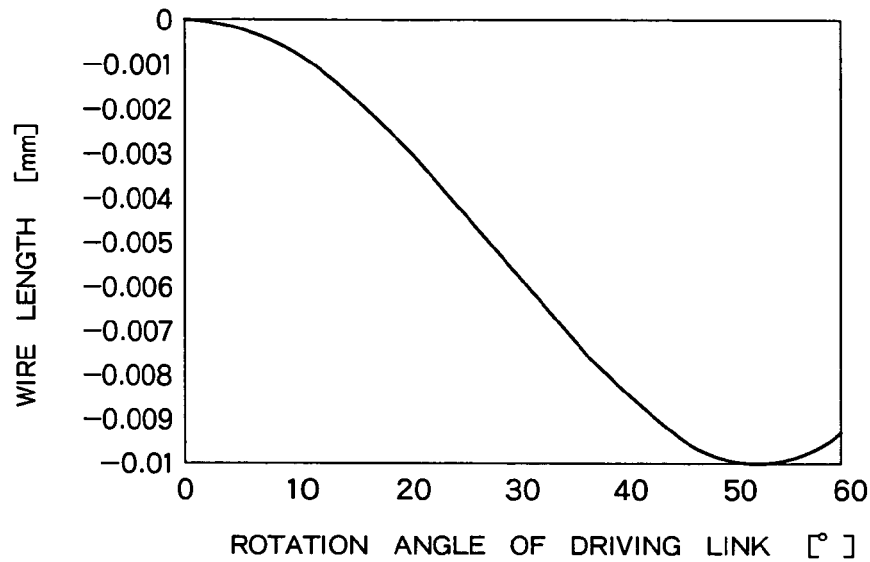
F I G. 10
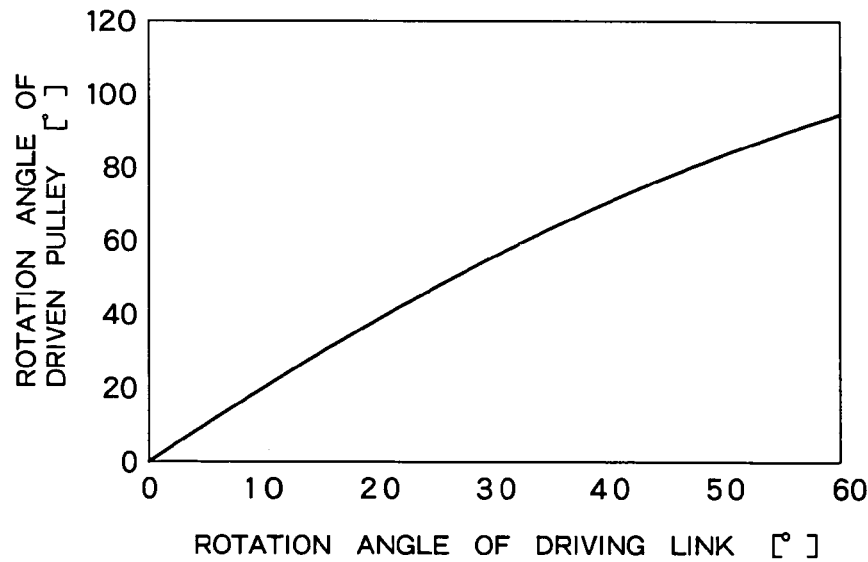
F I G. 11

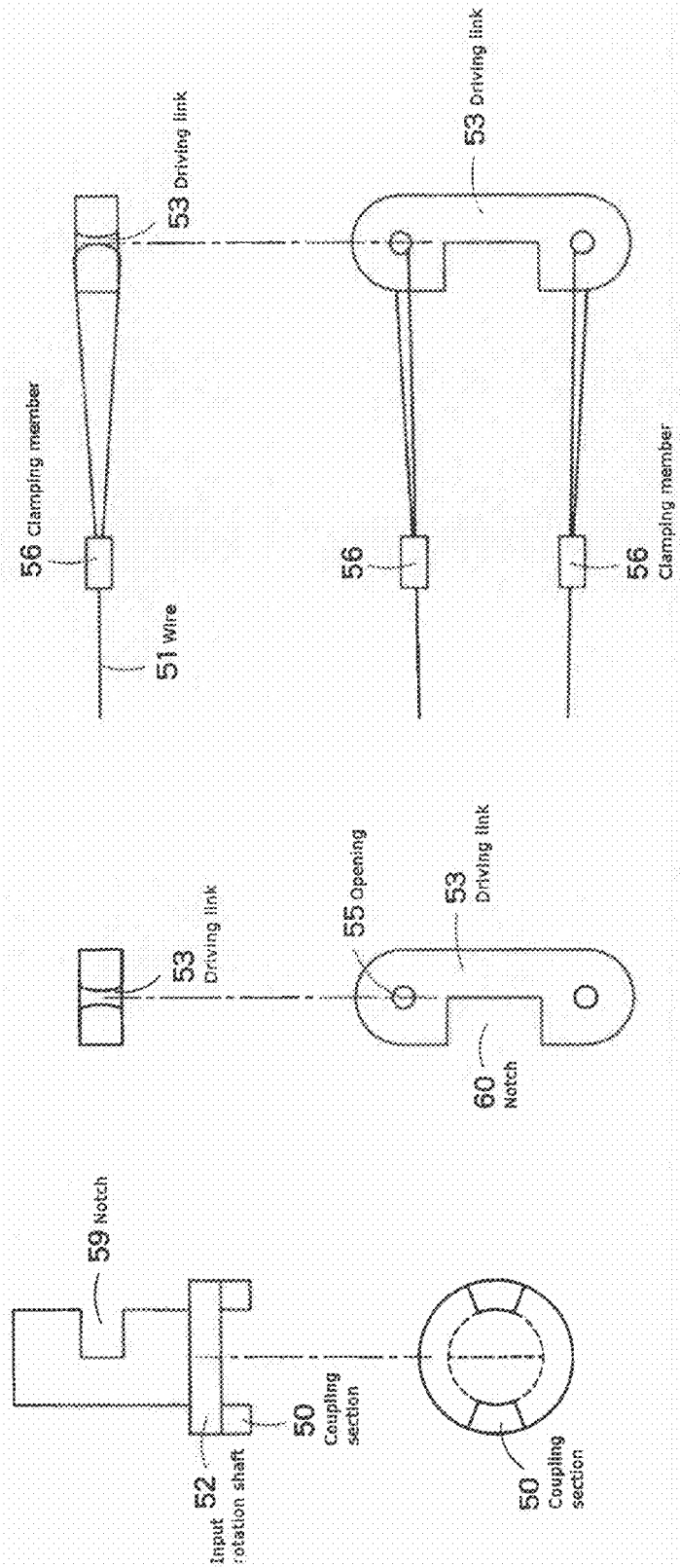

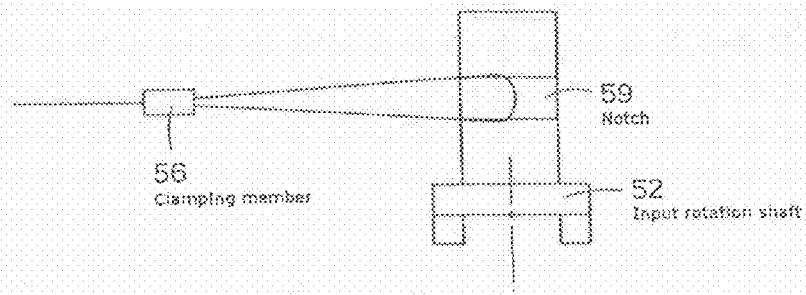
F I G. 13A
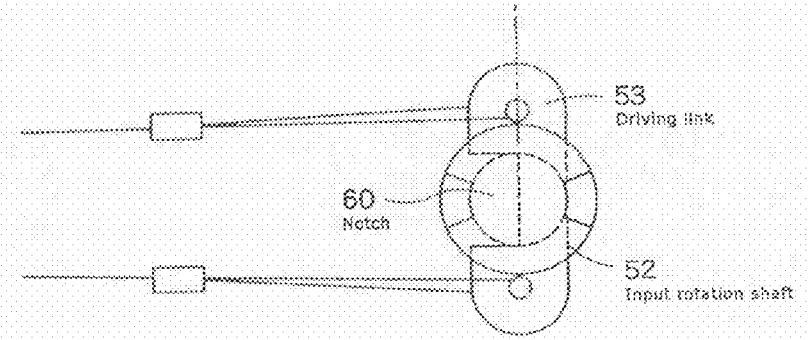
F I G. 13B
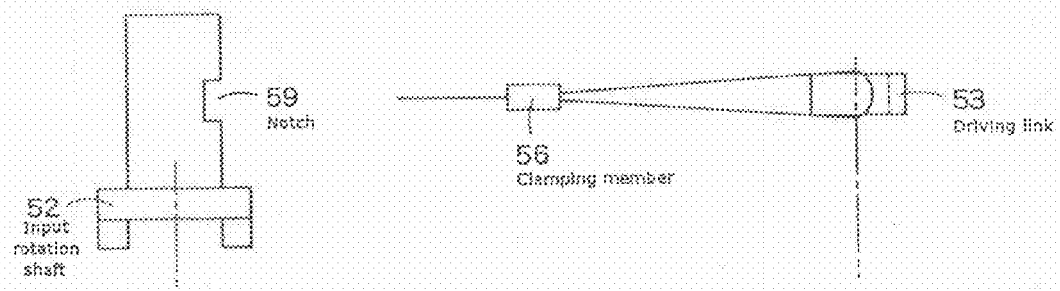
F I G. 14C        F I G. 14D
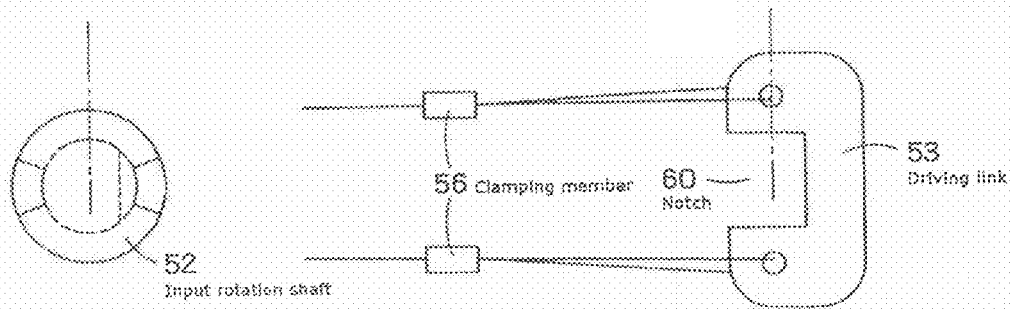
F I G. 14A        F I G. 14B

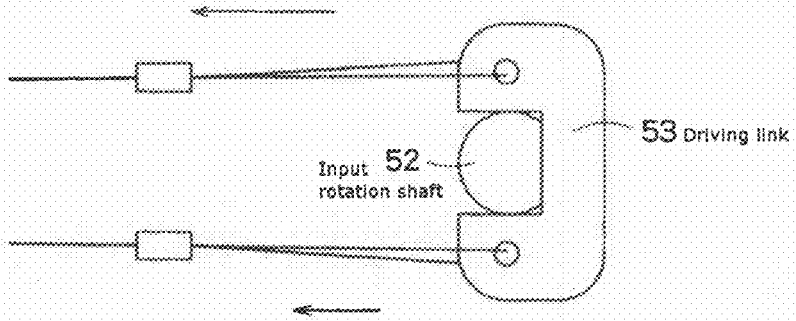
F I G. 15A
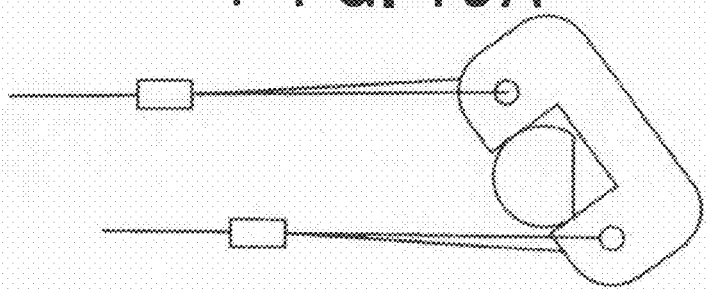
F I G. 15B
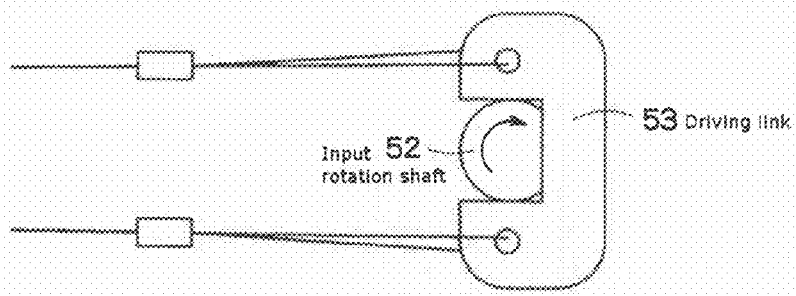
F I G. 16A
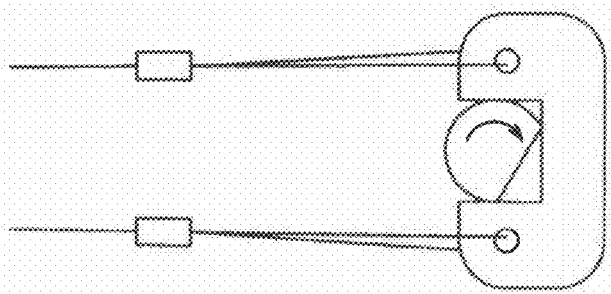
F I G. 16B

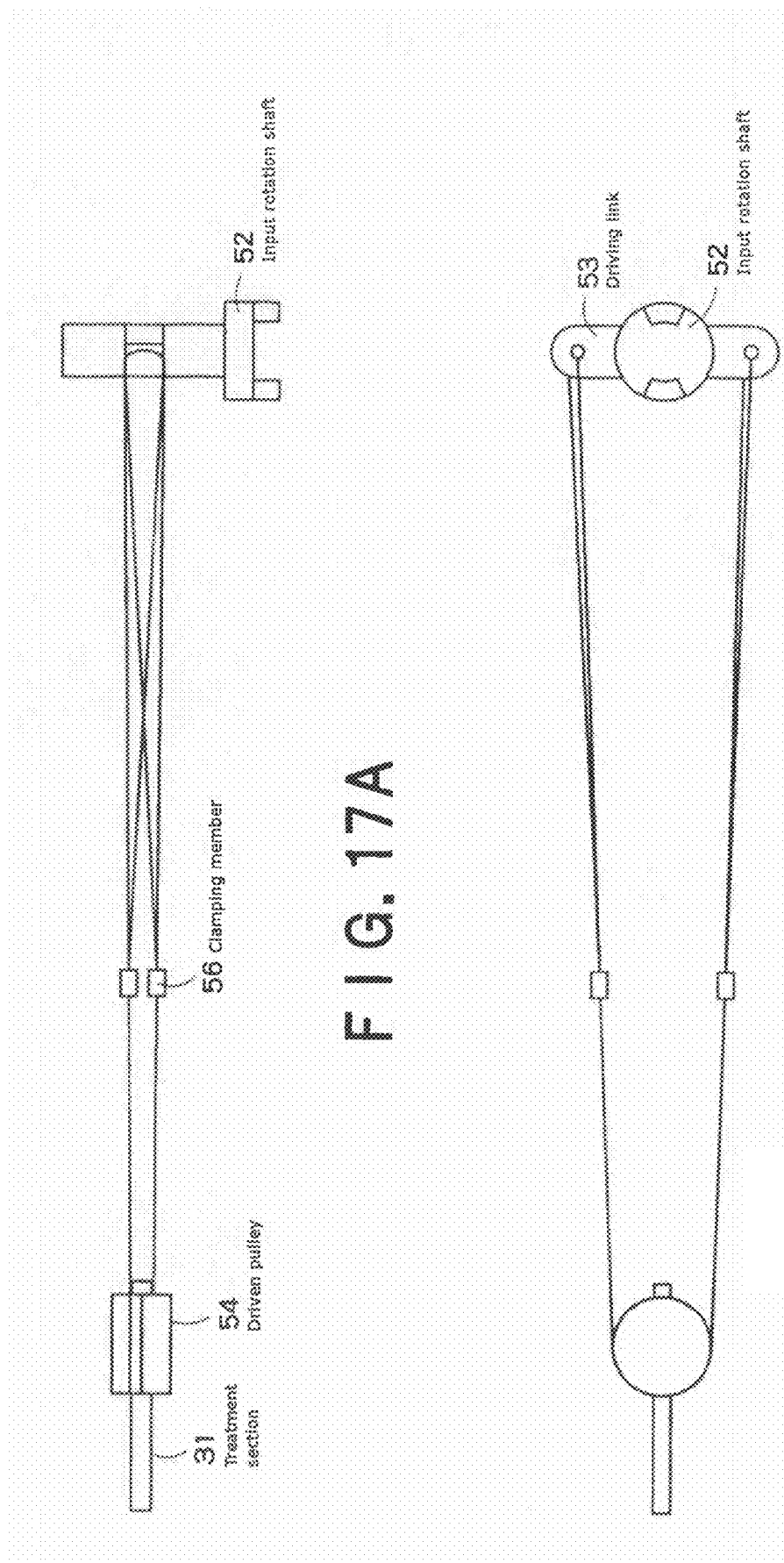

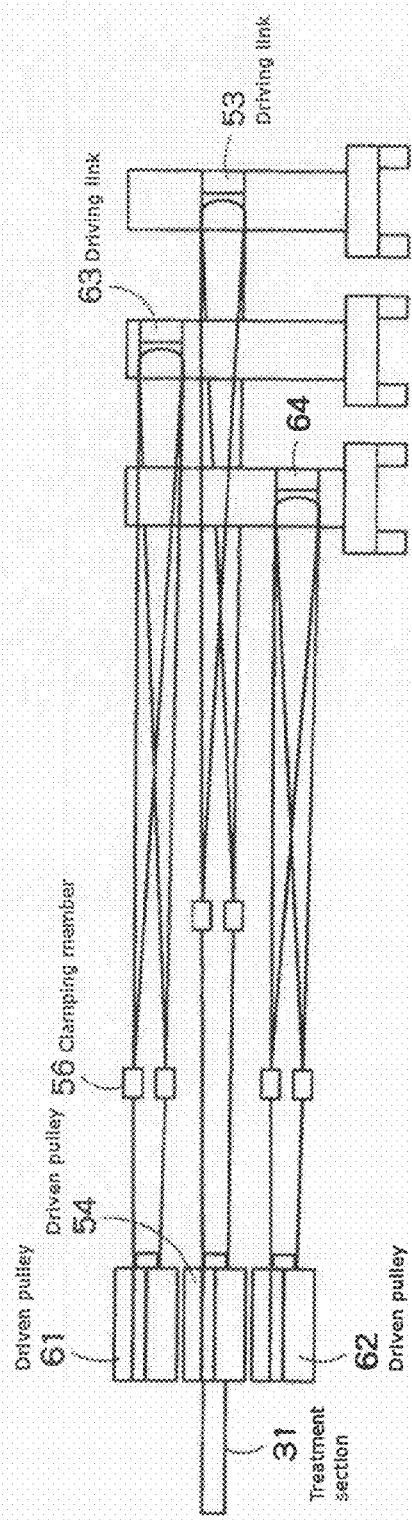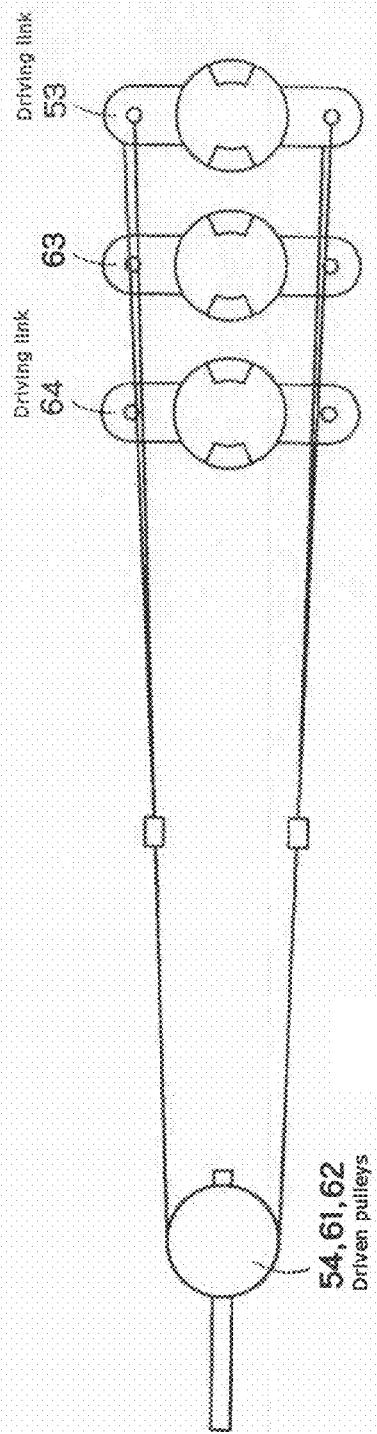
FIG. 18A
FIG. 18B

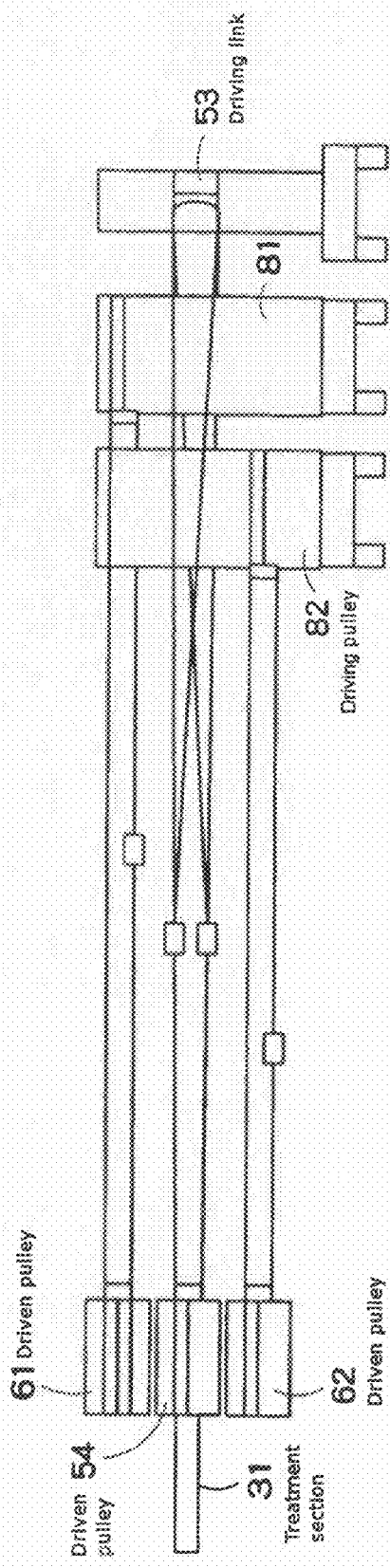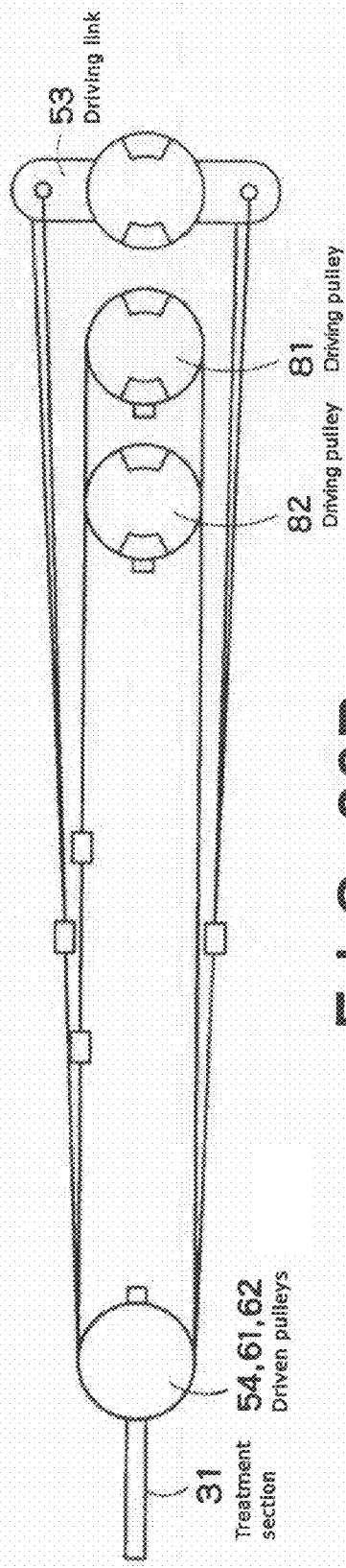
FIG. 20A
FIG. 20B

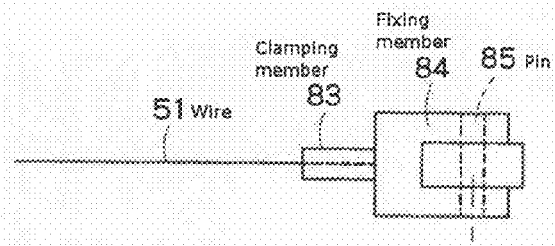
F I G. 21D
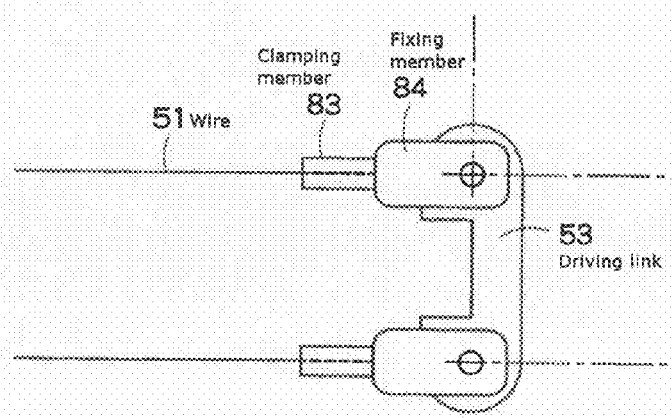
F I G. 21A
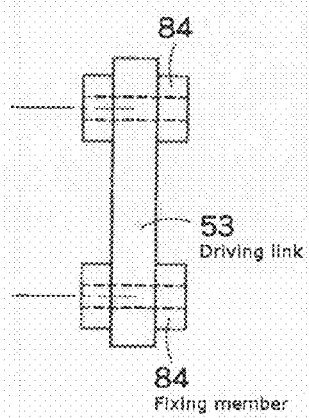
F I G. 21C
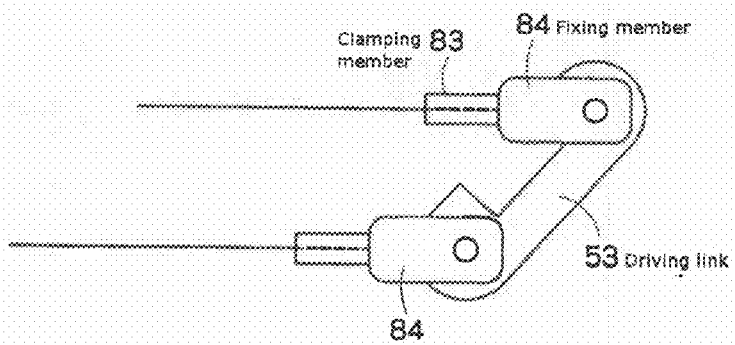
F I G. 21B

ROBOT AND MANIPULATOR

CROSS REFERENCE TO RELATED APPLICATIONS

This application is based upon and claims the benefit of priority from the prior Japanese Patent Application No. 2005-250076, filed on Aug. 30, 2005, the entire contents of which are incorporated herein by reference.

BACKGROUND OF THE INVENTION

1. Field of the Invention

The present invention relates to a robot and a manipulator that transmits mechanical power via a flexible power transmission member.

2. Related Art

There has been proposed a medical manipulator, such as robotic forceps for remotely operating surgical forceps (see Japanese Patent Laid-Open Pub. No. 2000-350735). Besides, there has been proposed a medical manipulator suitable for suture ligature (see Japanese Patent Laid-Open Pub. No. 2001-102248).

These conventional medical manipulators can be quickly manually operated by experts, and the experts can perform microscopic work by using them and can operate them from difficult angles. In particular, the manipulator has a bending or rotating joint at the tip thereof, so that the tip can be arbitrarily moved. Therefore, it is possible to easily perform suture and ligature from various directions, which are difficult for conventional forceps.

In addition, the robotic forceps can be used in combination with conventional surgical equipment. For example, an operator can use the robotic forceps with the right hand and a conventional forceps with the left hand. In addition, the robotic forceps themselves have a less complicated structure and require no expensive components, so that the robotic forceps has an advantage capable of fabricating it at low cost.

This kind of medical manipulator can be used for applications other than the medical application. For example, the manipulator is suitable for maintenance and repair at places where the operator cannot easily access, such as a narrow part of an energy device.

However, in the manipulators described in the above prior art documents, the manipulation section and the tip portion of the forceps are integrated with each other, and there are limitations on shape, dimensions and position of the power transmission mechanism between the manipulation section and the tip portion of the forceps.

Typically, a wire, a pulley or a link is used as the power transmission mechanism. For example, in a conventional power transmission mechanism using the wire and the pulley, if the diameter of the wire is small, or the distance between a driving pulley and a driven pulley is large, there arises a problem that elastic deformation (expansion) of the wire increases, and sufficient power transmission cannot be achieved. In addition, there is a problem that an adequate rotational rigidity cannot be achieved on the side of the driven shaft (output shaft) at a held state in which the driving pulley is fixed or at a servo lock state. If a desired rotational rigidity cannot be achieved, the intended operation cannot be carried out, and the operability and workability are reduced.

In addition, if an excessive load torque is imposed, the wire or a fastening part can be fractured. Furthermore, if the diameter of the pulley is not sufficiently larger than the diameter of the wire, a sufficient life cannot be obtained, and a fatigue fracture can occur. Furthermore, if the diameter of the pulley is sufficiently larger than the diameter of the wire, the power transmission mechanism becomes larger, and the rigidity thereof decreases.

On the other hand, in a conventional power transmission mechanism using a wire and a link, buckling of the link has to be taken into consideration. Thus, the link has to be sufficiently thick, or two links have to be disposed in parallel with each other. Accordingly, there are problems that the weight increases, and that a high component precision and a high assembly precision are required to dispose the links in parallel with each other. In addition, in the conventional power transmission mechanism using a link, the link cannot rotate to ±90 degrees, and thus, there is a problem that a sufficient range of movement cannot be ensured.

SUMMARY OF THE INVENTION

The present invention provides a robot and a manipulator that has a small size, a light weight, a simple structure, a high reliability and a high rigidity and can transmit mechanical power within a wide range of movement.

According to one embodiment of the present invention, a robot comprising:
a flexible power transmission member;
an input rotation axis rotated by a power generation source;
a driving link connected at both ends of the flexible power transmission member, which transmits a rotation torque of the input rotation axis to the flexible power transmission member; and
a driven pulley around which the flexible power transmission member is hung.

According to one embodiment of the present invention, a robot comprising:
a flexible power transmission member;
an input rotation axis rotated by a power generation source;
a driving link connected at one end of the flexible power transmission member, which transmits a rotation torque of the input rotation axis to the flexible power transmission member; and
a driven link connected at the other end of the flexible power transmission member, which has a length different from that of the driving link.

According to one embodiment of the present invention, a robot comprising:
a flexible power transmission member;
an input rotation axis rotated by a power generation source;
a driving pulley around which the flexible power transmission member is hung, which transmits a rotation torque of the input rotation axis to the flexible power transmission member; and
a driven link connected at both ends of the flexible power transmission member.

According to one embodiment of the present invention, a manipulator comprising:
a treatment section capable of being driven in two axes directions;
a working section which drives the treatment section in at least two axes directions;
a power transmission section which transmits power to the working section; and
a driving section which supplies power to the power transmission section,
wherein the power transmission section includes:
a flexible power transmission member;
an input rotation axis rotated by a power generation source;

a driving link connected at both ends of the flexible power transmission member, which transmits a rotation torque of the input rotation axis to the flexible power transmission member; and a driven pulley around which the flexible power transmission member is hung.

According to one embodiment of the present invention, a manipulator comprising:

a treatment section capable of being driven in two axes directions:

a working section which drives the treatment section in at lest two axes directions;

a power transmission section which transmits power to the working section; and a driving section which supplies power to the power transmission section, wherein the power transmission section includes:

a flexible power transmission member;

an input rotation axis rotated by a power generation source;

a driving link connected at one end of the flexible power transmission member, which transmits a rotation torque of the input rotation axis to the flexible power transmission member; and a driven pulley connected at the other end of the flexible power transmission member, which has a length different from that of the driving link.

According to one embodiment of the present invention, a manipulator comprising:

a treatment section capable of being driven in two axes directions:

a working section which drives the treatment section in at lest two axes directions;

a power transmission section which transmits power to the working section; and a driving section which supplies power to the power transmission section, wherein the power transmission section includes:

a flexible power transmission member;

an input rotation axis rotated by a power generation source;

a driving pulley around which the flexible power transmission member is hung, which transmits a rotation torque of the input rotation axis to the flexible power transmission member; and a driven link connected at both ends of the flexible power transmission member.

BRIEF DESCRIPTION OF THE DRAWINGS

FIG. 1A is a plan view of the power transmission mechanism, and FIG. 1B is a front view of the same.

FIG. 5 is a perspective view showing a configuration of the manipulator main unit 1 in detail.

FIGS. 8A and 8B are diagrams for illustrating an operation of the power transmission mechanism shown in FIGS. 1A and 1B.

FIG. 10 is a view showing relationship between rotation angle of the driving link 53 and a length of the wire 51.

FIG. 11 is a view showing relationship between the driving link 53 and rotation angle of the driven pulley.

FIGS. 12A-12C are diagrams showing structures of portions of the driving link 53 and the input rotation shaft 52.

FIGS. 13A and 13B are diagrams showing the notch 59 of the input rotation shaft 52 and the notch 60 of the driving link 53 engaged with each other.

FIGS. 14A-14D are diagrams showing an example in which the notch 60 of the driving link 53 is deeper than the notch 59 of the input rotation shaft 52.

FIGS. 15A and 15B are diagrams showing the notch 59 of the input rotation shaft 52 and the notch 60 of the driving link 53 shown in FIG. 14 engaged with each other.

FIGS. 16A and 16B are diagrams showing a case where the driven pulley 54 is locked, and the input rotation shaft 52 rotates.

FIGS. 17A and 17B are diagrams showing an example in which the clamping member 56 is located toward the driven pulley 54.

FIGS. 18A and 18B are diagrams showing a power transmission mechanism that can transmit mechanical power to the treatment section 31 shown in FIG. 5.

FIGS. 20A and 20B are diagrams showing an example in which two of three driven pulleys 54 are driven by driving pulleys 81 and 82.

FIGS. 21A-21D are diagrams showing a structure of the linkage section 4 between the fixing member 84 and the clamping member 83.

DETAILED DESCRIPTION OF THE INVENTION

In the following, embodiments of the present invention will be described with reference to the drawings.

First Embodiment

FIG. 1 includes diagrams showing a power transmission mechanism incorporated in a robot according to a first embodiment of the present invention. FIG. 1A is a plan view of the power transmission mechanism, and FIG. 1B is a front view of the same.

Figure 2:
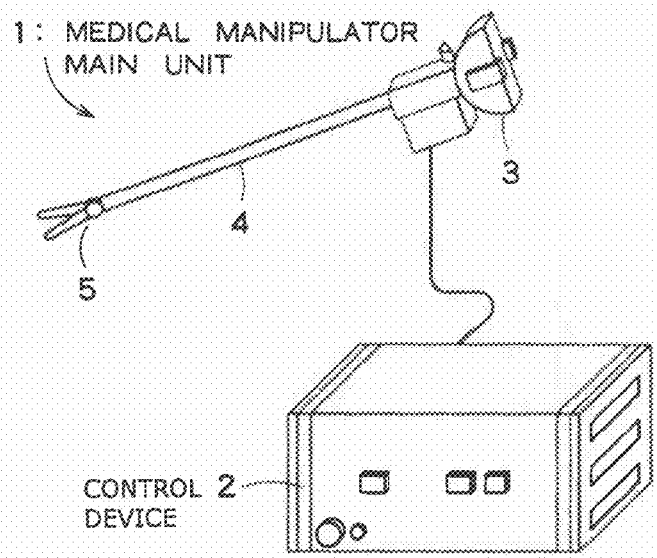
FIG. 2 is an external view of a robot that has a medical manipulator provided with the power transmission mechanism shown in FIGS. 1A and 1B.
Figure 3:
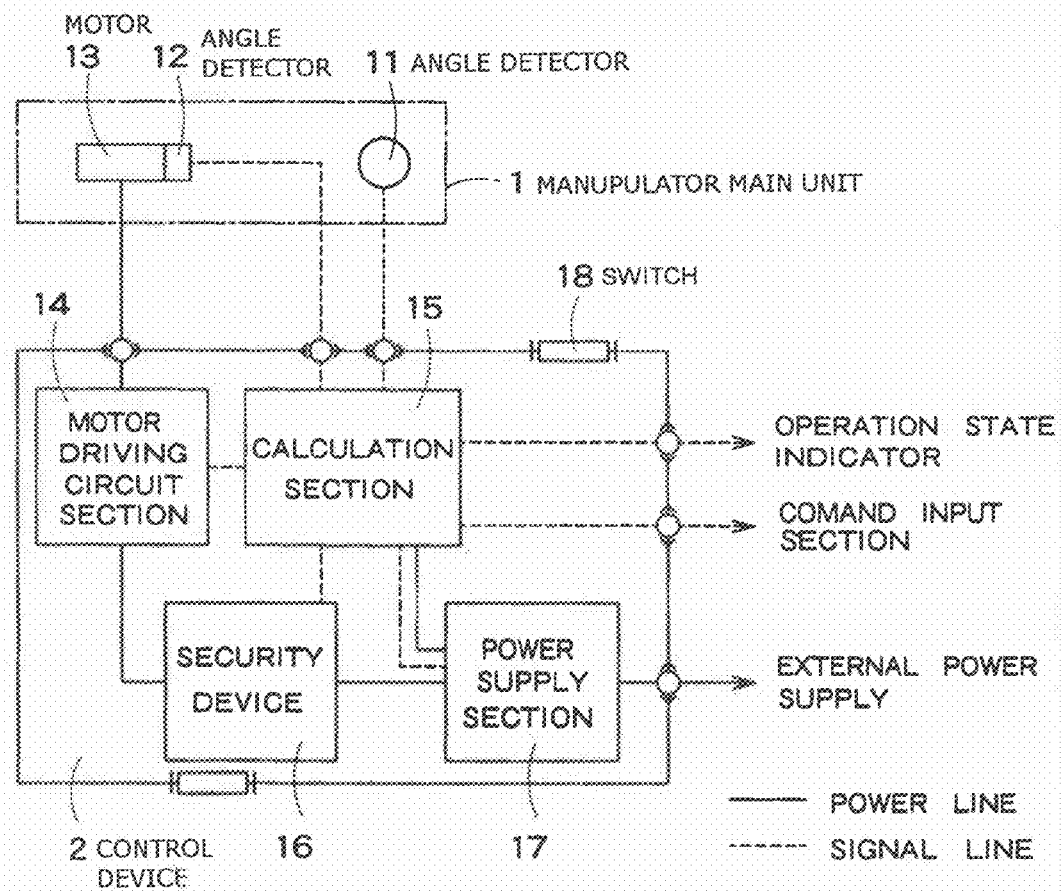
FIG. 3 is a block diagram showing an exemplary internal configuration of the medical manipulator system shown in FIG. 2.

The power transmission mechanism shown in FIGS. 1A and 1B is used for a robot, such as a medical manipulator. FIG. 2 is an external view of a robot that has a medical manipulator provided with the power transmission mechanism shown in FIGS. 1A and 1B (referred to as medical manipulator system hereinafter). FIG. 3 is a block diagram showing an exemplary internal configuration of the medical manipulator system shown in FIG. 2. The power transmission mechanism according to this embodiment is not exclusively applied to the medical manipulator described above but can be applied to a wide variety of manipulators of other configurations.

Prior to describing the power transmission mechanism shown in FIGS. 1A and 1B in detail, a configuration and an operation of the medical manipulator will be described with reference to FIGS. 2 and 3. The medical manipulator system has a medical manipulator main unit 1 and a control device 2. The manipulator main unit 1 has a manipulation section 3 for manipulation by an operator, a linkage section 4 incorporating part of the power transmission mechanism shown in FIGS. 1A and 1B, and a working section 5 that works at a site of work (operation site). The manipulation section 3 has an angle detector 11 that detects the amount and direction of manipulation by the operator, and the working section 5 has an angle detector 12 that detects the angle of a treatment section described later and a motor 13 that drives the treatment section.

The control device 2 has a motor driving circuit section 14 that controls the driving of the motor, a calculation section 15 that calculates the amount and direction of driving of the motor based on detection signals from the angle detectors 11 and 12, a security device 16 that blocks the current to the motor depending on the situation, a power supply section 17 and a switch 18 for various manipulation commands. The phrase "depending on the situation" means a case where the robot has to be prevented from being damaged, or a working target worked at a site to be worked has to be protected, such as a case where an emergency stop switch on the control device 2 is manipulated.

Figure 4:
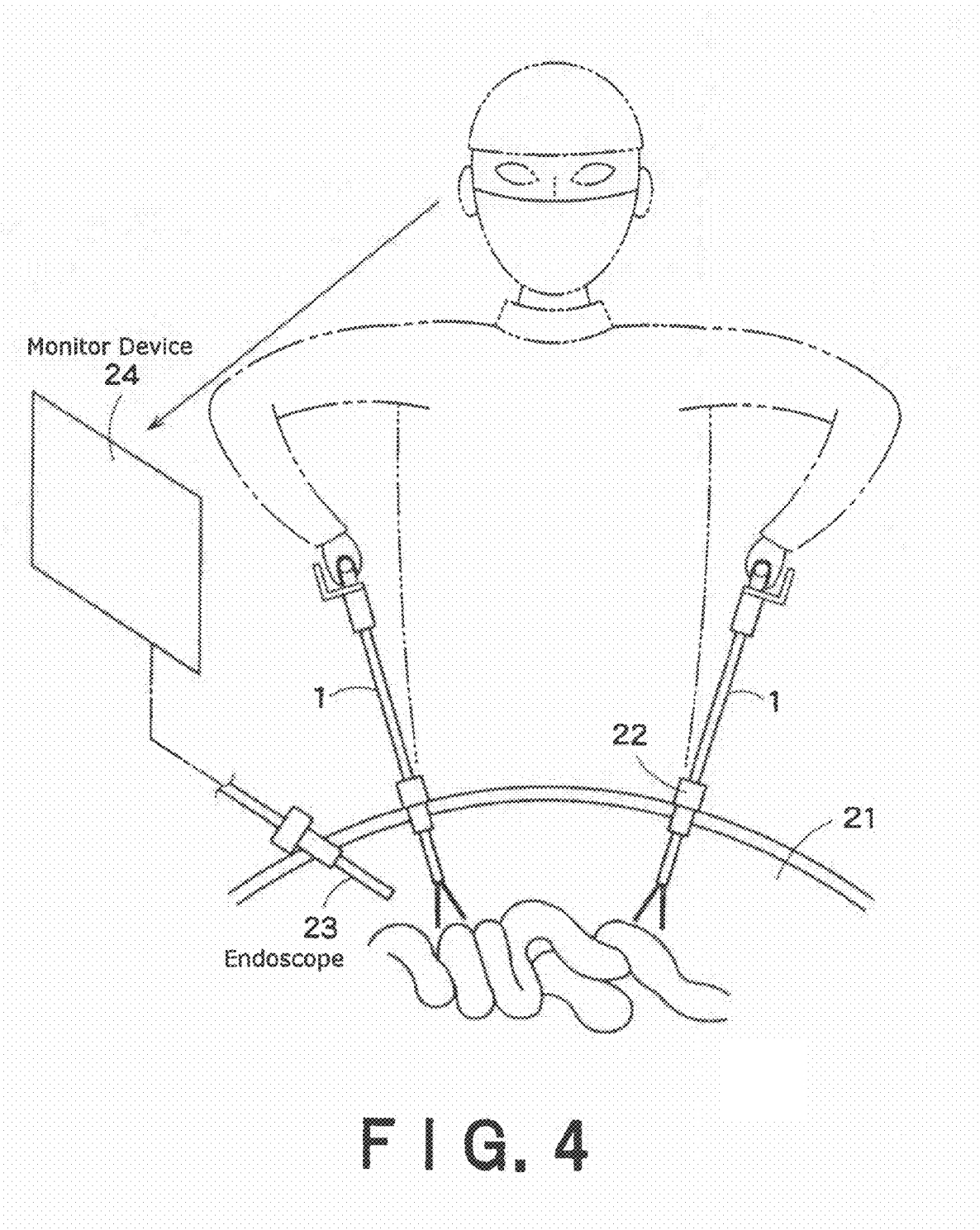
FIG. 4 is a diagram for illustrating laparoscopic surgery.

FIG. 4 is a diagram for illustrating laparoscopic surgery, such as cholecystectomy, carried out using the manipulator shown in FIGS. 1A and 1B. As shown in this drawing, a plurality of small openings are formed in an abdomen 21 of a patient, and a trocar 22 is attached to each opening. An endoscope 23, the manipulator 1 or the like is inserted in each opening through the trocar 22, and an operator (typically a surgeon) carries out surgery by observing the endoscopic image displayed on a monitor device 24. This method of surgery involves no laparotomy, so that the burden on the patient is reduced, and the number of days required for recover from surgery and a period for hospitalization is significantly reduced.

FIG. 5 is a perspective view showing a configuration of the manipulator main unit 1 in detail. The working section 5 has a treatment section 31 that perform a treatment on an operation section and supporting sections 32 and 33. The supporting section 32 has a rotation axis (a first rotation axis "a1") perpendicular to the central axis of the linkage section 4 around which the treatment section 31 rotates in a direction ("y1" direction). The supporting section 33 has a rotation axis (a second rotation axis "a2") perpendicular to the first rotation axis, in conformity to the central axis of the linkage section 4 around which the treatment section 31 rotates in a direction ("y2" direction). These rotation axes enable the treatment section 31 to rotate in two directions perpendicular to each other. In addition, the treatment section 31 can perform a holding operation in an "y3" direction as described later.

The manipulation section 3 is a section that the operator manipulates by hand, and has a posture control section 34 and a treatment operation section 35. The posture control section 34 has a third rotation axis "a3" perpendicular to the central axis of the linkage section 4 and a fourth rotation axis "a4" perpendicular to the third rotation axis. The operator manipulates the treatment operation section 35 by his or her fingers to achieve the rotational operations around the third and fourth rotation axes and the holding operation.

The direction of manipulation by the operator coincides with the rotational direction of the treatment section 31, so that the operator can make the treatment section 31 rotate without sense of discomfort.

Operational information of the treatment operation section 35 by the operator is obtained by the angle detector 11 and sent to the control device 2. Based on the operational information about the treatment operation section 35, the control device 2 drives driver sections 36 to 38, thereby actuating the power transmission mechanism. The power transmission mechanism is incorporated in a linkage end portion 40 on the top of the driver sections 36 to 38, the linkage section 4 and the working section 5.

The linkage section 4 is supported by a supporting mechanism 39. The supporting mechanism 39 has a position adjustment mechanism 41 that moves vertically and horizontally with respect to a base portion and an arc arm 42 that moves along the same vertical axis as the base portion and along the linkage section 4.

Now, a configuration and an operation of the power transmission mechanism will be described with reference to FIGS. 1A and 1B. The power transmission mechanism shown in FIGS. 1A and 1B has a flexible power transmission member 51, an input rotation shaft 52, a driving link 53 and a driven pulley 54. The driving link 53 is provided on the linkage end portion 40 shown in FIG. 5, the flexible power transmission member 51 is provided on the linkage section 4, and the driven pulley 54 is provided on the working section 5 or the supporting section 32.

An example of the flexible power transmission member 51 is a wire 51. The driving link 53 has openings 55, through each of which the wire 51 passes. The openings 55 are formed at the longitudinal ends thereof. The wire 51 is passed through the opening 55 and secured by a clamping member 56. The input rotation shaft 52 is attached at the center of the driving link 53. Rotation of the rotation shaft causes the driving link 53 to rotate, thereby generating a tension to pull the wires in the longitudinal direction. The internal edge of the opening 55 is chamfered in a tapered shape or in the shape of the letter "R" in order to prevent the wire 51 from being damaged and facilitate smooth passage of the wire 51. Since the wire 51 is hung through the opening 55, the wire 51 is doubled, so that the stress exerted on the wire 51 can be halved from the tension required for driving. Therefore, compared with the case where the wire 51 is not doubled, the fatigue life of the wire 51 can be elongated, and the strength and reliability of the wire 51 can be increased. In addition, if the wire is hung around a pulley, the part of the wire hanging around the pulley is repeatedly subjected to a bending stress, so that a problem with the fatigue life may arise. However, according to this embodiment, the part of the wire 51 on the side of the input rotation shaft 52 is not subjected to any repeated bending stress, so that the reliability of the wire 51 is increased.

The input rotation shaft 52 is coupled directly to a motor shaft or an output shaft of a decelerator (not shown) or coupled to the motor shaft or the like via a coupling section 50. The rotational torque of the input rotation shaft 52 is transmitted directly to the driving link 53.

The wire 51 is hung through the driven pulley 54. While only one wire 51 extends in the direction from the claming member 56 to the driven pulley 54, two wires 51 extend in the direction from the clamping member 56 to the driving link 53.

Figure 6:
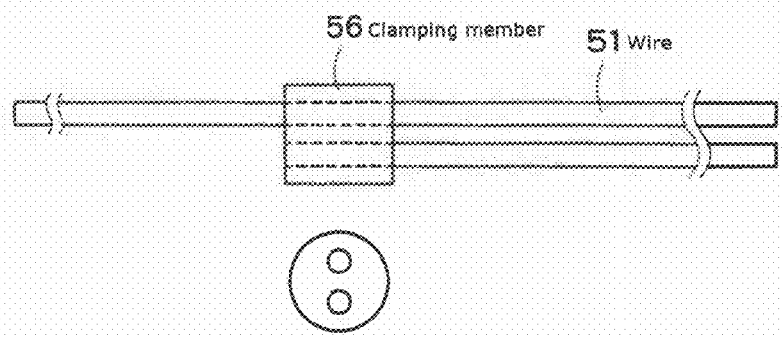
FIG. 6 is a plan view of the clamping member 56.

FIG. 6 is a plan view of the clamping member 56. The clamping member 56 has openings for receiving wires 51 and secures the wires 51 inserted in the openings. By providing the claming member 56, the length of the wire 51 from the clamping member 56 to the driving link 53 is kept constant.

Figures 7A, 7B, 7C:
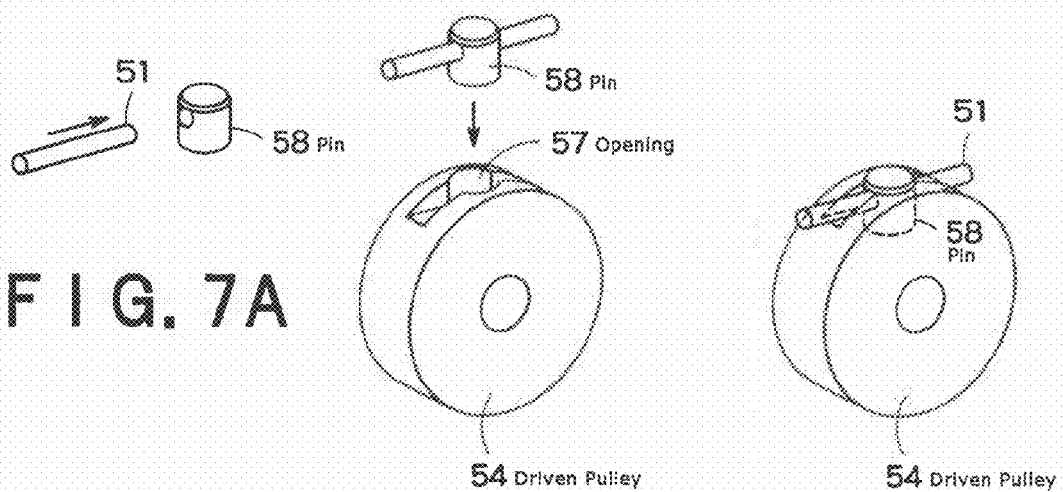
FIGS. 7A-7C are enlarged perspective views of the driven pulley 54.

FIG. 7 is an enlarged perspective view of the driven pulley 54. As shown in this drawing, the driven pulley 54 has an opening 57 in the outer surface thereof, and a pin 58 through which the wire 51 is passed is inserted in the opening 5.7 (see FIGS. 7A and 7B). Therefore, a wedge effect is obtained, and the wire 51 is firmly secured to the driven pulley 54.

FIG. 8 includes diagrams for illustrating an operation of the power transmission mechanism shown in FIGS. 1A and 1B. As shown in FIG. 8A, if the input rotation shaft 52 rotates in the "A" direction as indicated by the arrow, the driving link 53 also rotates in the "A" direction, the mechanical power is transmitted to the driven pulley 54 via the wire 51, and the treatment section 31 rotates in the "A" direction. In addition, as shown in FIG. 8B, if the input rotation shaft 52 rotates in the "B" direction as indicated by the arrow, the treatment section 31 rotates in the "B" direction.

In the case shown in FIG. 8, as the driving link 53 rotates, the length of the wire 51 is not geometrically constant in a strict sense but varies slightly because of the tension thereof. However, if the distance (center distance) between the driving link 53 and the driven pulley 54 is sufficiently longer than the diameter of the pulley and the length of the link, the variation of the length of the wire 51 can be substantially ignored and has little effect on the performance.

Figure 9:
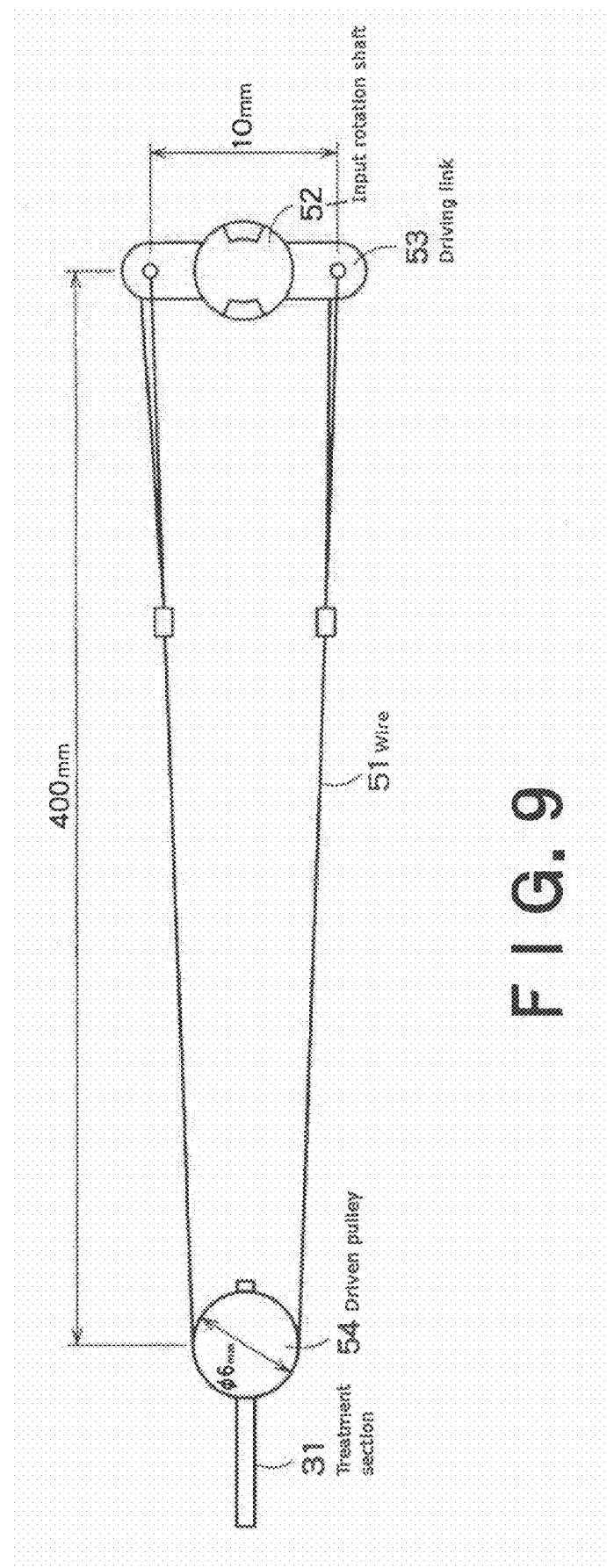
FIG. 9 is a plan view of the power transmission mechanism in which a length of the driving link is 10 mm, a diameter of the driven pulley is 6 mm and a distance between axes is 400 mm.

For example, if assumed that the length of the driving link 53 is 10 mm, the diameter of the driven pulley 54 is 6 mm, and the center distance is 400 mm as shown in FIG. 9, the relationship between the rotation angle of the driving link 53 and the variation in length of the wire 51 is as shown in FIG. 10, and the relationship between the rotation angles of the driving link 53 and the driven pulley 54 is as shown in FIG. 11.

As shown in these drawings, while the driving link rotates 60 degrees, the length of the wire 51 changes by 0.01 mm. Considering the diameter of the wire 51 determined by the diameter of the pulley (that is, the bend radius of the wire 51) and the elastic modulus of the wire, that is, considering the elastic deformation of the wire, the change in length of the wire 51 does not adversely affect the power transmission.

In addition, while the rotation angle range of the driving link 53 is ±60 degrees, the driven pulley 54 can rotate within a wider angle range of about ±100 degrees. This rotation angle ratio approximately corresponds to the ratio between the length of the driving link 53 and the diameter of the driven pulley 54. Therefore, by making the length of the driving link 53 larger than the diameter of the driven pulley 54, a sufficient movement range of the driven pulley 54 can be ensured.

FIG. 12 includes diagrams showing structures of portions of the driving link 53 and the input rotation shaft 52 that are to be engaged with each other. FIG. 12A includes a plan view and a front view of the input rotation shaft 52, FIG. 12B is a plan view and a front view of the driving link 53, and FIG. 12C is a plan view and a front view of the driving link 53 through which the wires 51 are hung. As shown, the internal edge of the opening 55 of the driving link 53 is chamfered in the shape of the letter "R".

The input rotation shaft 52 has a notch 59, and the driving link 53 also has a notch 60.

FIG. 13A shows the notch 59 of the input rotation shaft 52 engaged with each other and FIG. 13B shows the notch 60 of the driving link 53 engaged with each other, in which end faces of the notches 59 and 60 are indicated by a dotted line. Since a restoring force is exerted on the wire 51 due to the elastic deformation even in the initial state, the notch 60 of the driving link 53 can be firmly pressed against the notch 59 of the input rotation shaft 52, and the rotational torque can be stably transmitted simply by engaging the notches with each other.

By appropriately adjusting the depth of at least one of the notch 59 of the input rotation shaft 52 and the notch 60 of the driving link 53, it is possible to be used as a mechanical fuse which disengages the notches in response to an excessive torque larger than a predetermined amount exerted on the input rotation shaft 52 and the driving link 53.

FIG. 14 includes diagrams showing an example in which the notch 60 of the driving link 53 is deeper than the notch 59 of the input rotation shaft 52. FIG. 14A is a front view of the input rotation shaft 52, FIG. 14C is a plan view of the input rotation shaft 52, FIG. 14B is a front view of the driving link 53, and FIG. 14D is a plan view of the driving link 53.

FIG. 15 shows the notch 59 of the input rotation shaft 52 and the notch 60 of the driving link 53 shown in FIG. 14 engaged with each other. FIGS. 15A and 15B show a state where the input rotation shaft 52 is locked, and an excessive load is exerted on the driven pulley 54. In this case, the input rotation shaft 52 and the driving link 53 do not move (there may be a slight movement due to the elastic deformation of the wire) until a predetermined load is given. Once the load exceeds the predetermined amount, only the driving link 53 rotates but the input rotation shaft 52 does not rotate. Thus, the mechanical fuse is activated.

On the other hand, FIGS. 16A and 16B show a case where the driven pulley 54 is locked, and the input rotation shaft 52 rotates. In this case, the input rotation shaft 52 does not rotate (there may be a slight movement due to the elastic deformation of the wire) until a predetermined rotational load is given. Once the rotational load exceeds the predetermined amount, only the input rotation shaft 52 rotates but the driving link 53 does not rotate. Again, the mechanical fuse is activated.

Such a mechanical fuse can readily recover its original state when the overload is removed, prevent the system from being damaged by any overload, and improve the safety and reliability of the power transmission mechanism. In addition, even if the driving link 53 is overloaded when the driven pulley 54 is locked, it does not cause abnormal operation of the driven pulley 54. Thus, the worked target can be prevented from being adversely affected, and high safety is ensured.

The load torque that activates the mechanical fuse can be determined by the shape and depth of the notches of the driving link 53 and the input rotation shaft 52, the supporting position, tensile rigidity and initial tension of the wire 51, and the like.

Referring to FIGS. 1A and 1B, the clamping member 56 disposed between the driving link 53 and the driven pulley 54 is located toward the driving link 53 from the center. To the contrary, FIG. 17 shows an example in which the clamping member 56 is located toward the driven pulley 54. In this case, a longer section of wire 51 is doubled, and the tensile rigidity of the wire 51 is increased compared with the case shown in FIGS. 1A and 1B. As a result, the indirect rigidity of the driven pulley 54 can be increased.

In FIGS. 1A and 1B, the treatment section 31 can rotate around only one axis. However, the treatment section 31 of the medical manipulator shown in FIG. 5 can rotate around two axes and perform a holding operation. FIG. 18 includes diagrams showing a power transmission mechanism that can transmit mechanical power to the treatment section 31 shown in FIG. 5. FIG. 18A is a plan view, and FIG. 18B is a front view.

The power transmission mechanism shown in FIG. 18 has driven pulleys 54, 61 and 62 that rotate the treatment section 31 in the directions indicated by the arrows "y1", "y2" and "y3" in FIG. 5. Wires 51 are hung around the three driven pulleys 54, 61 and 62 individually, and the ends of each wire 51 are connected to its corresponding driving link 53, 63 or 64. The input rotation shafts mounted on the driving links 53, 63 and 64 are independently rotationally driven. Therefore, the three driven pulleys 54, 61 and 62 rotate independently.

If the clamping members 56 are attached to the wires 51 at the same longitudinal positions, the clamping members 56 can come into contact with each other. Thus, as shown in FIG. 18A, the clamping members 56 vertically adjacent to each other are preferably staggered in the longitudinal direction of the wires 51. If possible, it is preferable that not only the adjacent clamping members but also all the clamping members are staggered in the longitudinal direction to each other.

Figure 19:
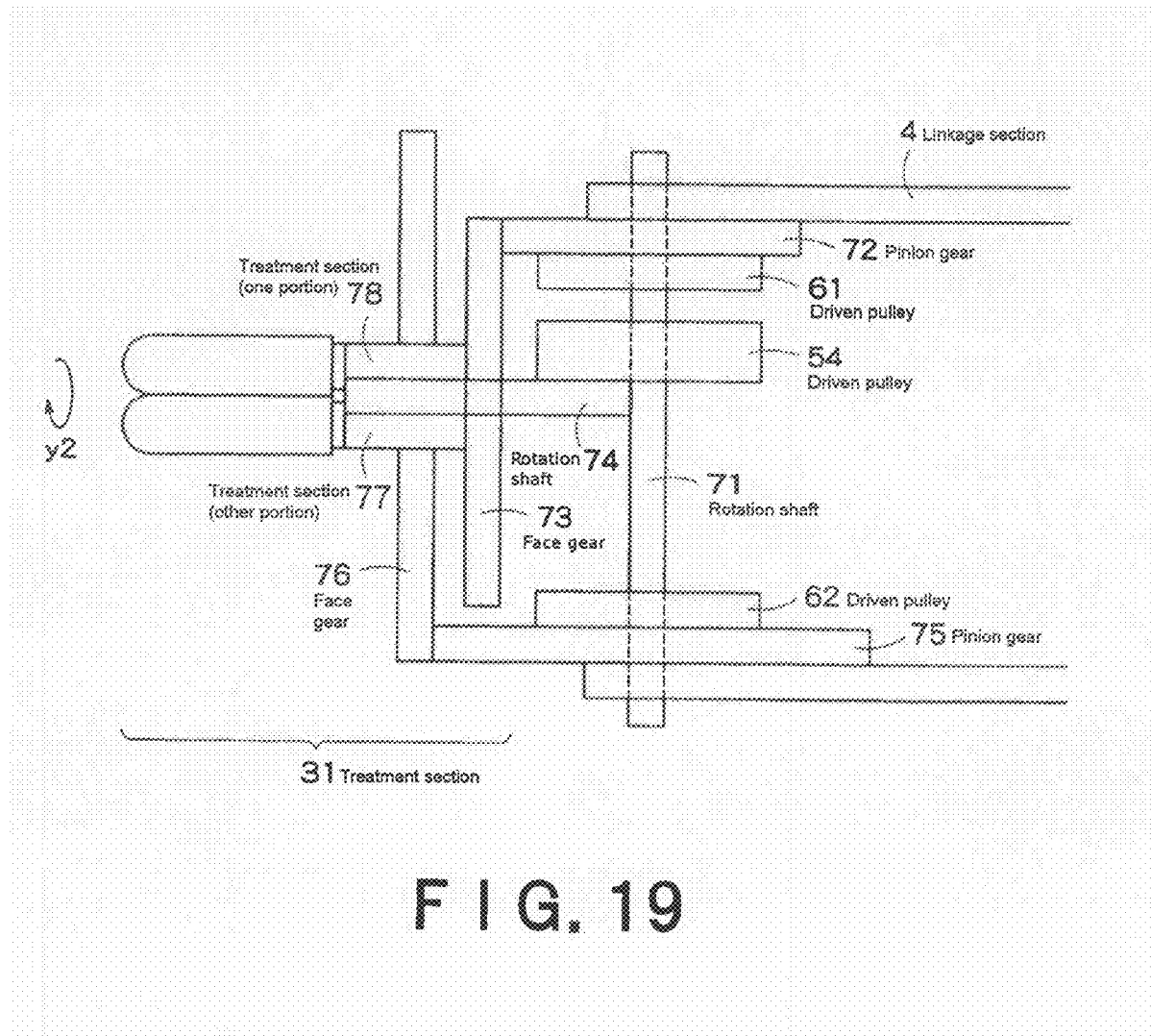
FIG. 19 is a plan view showing the structure between the driven pulley 54 and the treatment section 31 in detail.

Although not shown in FIG. 18, between the three driven pulleys 54, 61 and 62 and the treatment section 31, there is provided a mechanism that switches the drive direction. FIG. 19 is a plan view showing the structure between the driven pulley 54 and the treatment section 31 in detail. As shown in this drawing, the driven pulley 54 is rotatably supported on a rotation shaft 71, and the treatment section 31 rotates in the direction indicated by the arrow "y1" in FIG. 5 in conformity to rotation of the rotation shaft 71 on which the rotation shaft 74 is fixed.

The driven pulley 61 is rotatably supported on the rotation shaft 71. A pinion gear 72 is coaxially fixed to the driven pulley 61 and engaged with a face gear 73 that is positioned perpendicularly to the pinion 72. The face gear 73 is rotatably supported on the rotation shaft 74, and one portion 78 of the treatment section 31 is fixed to the face gear 73.

The driven pulley 62 is also rotatably supported on the rotation shaft 71. A pinion gear 75 is coaxially fixed to the driven pulley 62 and engaged with a face gear 76 that is positioned perpendicularly to the pinion gear 75. The face gear 76 is rotatably supported on the rotation shaft 74, and the other portion 77 of the treatment section 31 is fixed to the face gear 76.

Therefore, if the driven pulleys 61 and 62 are driven in the opposite directions, the treatment section 31 rotates in the direction indicated by the arrow "y2", and if the driven pulleys 61 and 62 rotate in the same direction, the treatment section 31 performs the holding operation.

FIG. 18 shows an example in which the three driven pulleys 54, 61 and 62 are driven by the separate driving links 53, 63 and 64. However, a driving pulley may be used to drive at least some of the driven pulleys. FIG. 20 shows an example in which two of three driven pulleys 54 are driven by driving pulleys 81 and 82, and the remaining one driven pulley 54 is driven by the driving link 53. If a link is used for driving, the wire 51 can be doubled, so that the life of the wire 51 is elongated. However, the structure is more complicated than the structure that uses a pulley for driving. Thus, in the case of the power transmission mechanism shown in FIG. 20, it is preferable that a pulley is used for the driving part having a low load, and a link is used for the driving part having a high load.

With reference to FIGS. 1A and 1B and the like, there has been described an example in which the wires 51 is hung through the openings 55 formed in the driving link 53 to double the wires 51. However, as shown in FIGS. 21A and 21B, a clamping member 83 and an engaging member 84 that engages the clamping member 83 with the driving link 53 may be attached to each end of the wire 51 depicted in FIGS. 1A and 1B.

FIG. 21 includes diagrams showing a structure of the linkage section 4 between the fixing member 84 and the clamping member 83. FIG. 21A includes a front view of the structure, FIGS. 21C and 21D are plan views thereof from different directions, and FIG. 21B is a front view of the structure with the wire 51 being loaded.

The fixing member 84 has the clamping member 83 and is rotatably coupled to the driving link 53 by a pin 85 inserted in an insertion hole formed at the end thereof opposite to the clamping member 83. The fixing member 84 can rotate about the pin 85. Therefore, if the wire 51 is loaded as shown in FIG. 21B, the fixing member 84 rotates with respect to the driving link 53, so that the fixing member 84 can be prevented from being subjected to an excessive tension and thus prevented from being fractured.

As described above, according to the first embodiment, the driving link 53 and the driven pulley 54 are connected by the wire 51, and the part of the wire 51 connected to the driving link 53 is doubled, or the wire 51 is fixed to the driving link 53 by the clamping member 83 and the fixing member 84. Therefore, even when a high load is exerted on the driving link 53, the wire 51 is unlikely to break, and the reliability and safety are increased. In addition, since a mechanical fuse is formed at the engaged portion between the driving link 53 and the input rotation shaft 52, the working section 5 can be prevented from being subjected to an abnormal load, so that the safety is increased. Furthermore, since a plurality of power transmission mechanisms according to this embodiment can be stacked vertically, the power transmission mechanism can be easily applied to a manipulator that involves a plurality of rotational operations in different directions and a holding operation. Furthermore, since the power transmission mechanism can be downsized, it can be applied to a medical manipulator or the like that involves precise operations.

Second Embodiment

According to the first embodiment described above, the length of the driving link 53 is larger than the diameter of the driven pulley 54. However, there is no particular limitation on the relationship between these two dimensions, and the dimensions may be changed as required.

Figure 22:
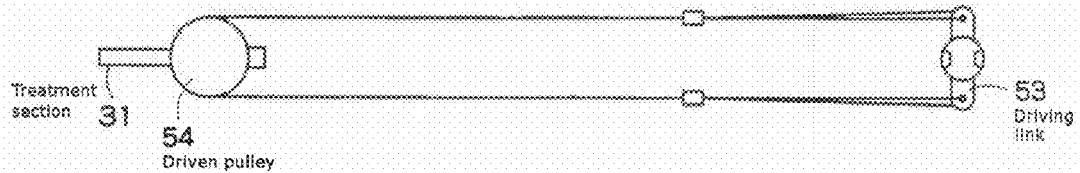
FIG. 22 is a diagram showing a power transmission mechanism in which the diameter of the driven pulley 54 is equal to the length of the driving link 53.
Figure 23:
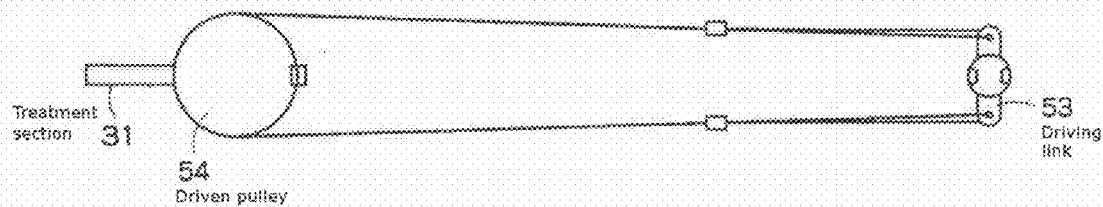
FIG. 23 is a diagram showing a power transmission mechanism having a reduction ratio larger than 1.

For example, FIG. 22 shows a power transmission mechanism in which the diameter of the driven pulley 54 is equal to the length of the driving link 53, that is, the reduction ratio is 1. FIG. 23 shows a power transmission mechanism having a reduction ratio larger than 1. In any case, the power transmission mechanism has the same structure as the structure according to the first embodiment except for having the different reduction ratio. The reduction ratio can be appropriately determined taking into consideration various conditions including the specific operation of the treatment section 31, the size and range of movement of the power transmission mechanism, the rigidity of the wire 51 or the like.

The power transmission mechanism described above with reference to FIGS. 1A and 1B and the like has a driving link 53 and a driven pulley 54. However, the present invention can be applied to a power transmission mechanism that has a driving pulley and a driven link.

Figure 24:
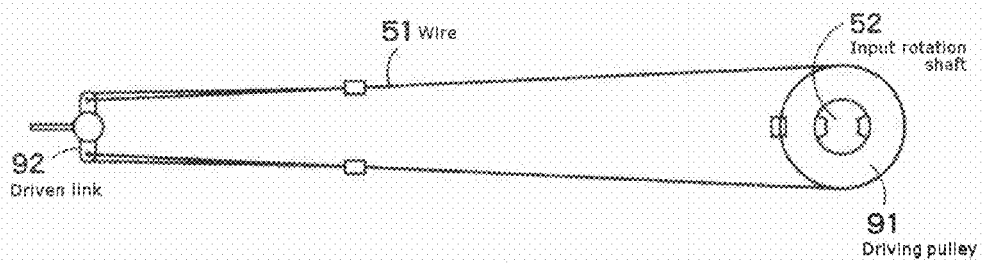
FIG. 24 is a diagram showing a case in which the reduction ratio is less than 1.
Figure 25:
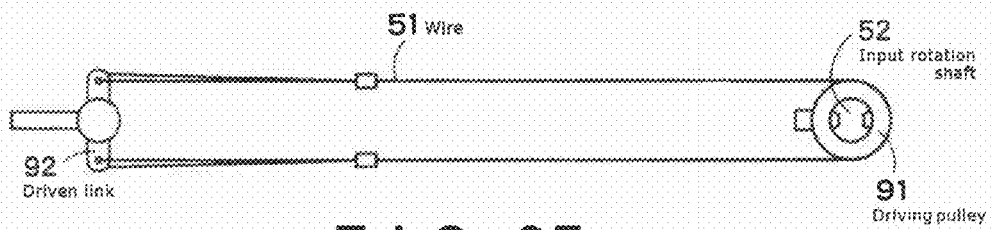
FIG. 25 is a diagram showing a case in which the reduction ratio is 1.
Figure 26:
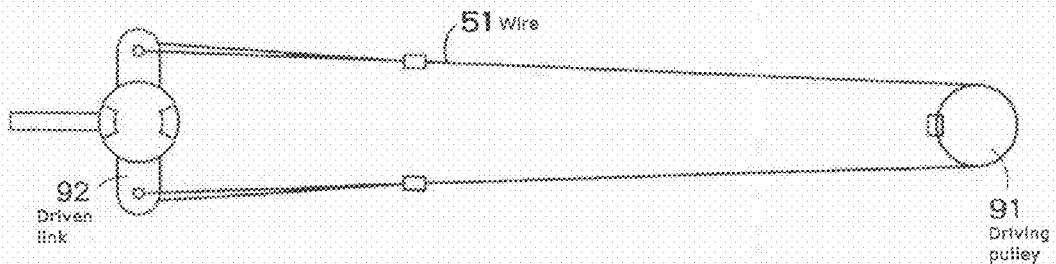
FIG. 26 is a diagram showing a case in which the reduction ratio is larger than 1.

FIGS. 24, 25 and 26 are front views showing examples of a power transmission mechanism that has a driving pulley 91 and a driven link 92. FIG. 24 shows a case in which the reduction ratio is less than 1, FIG. 25 shows a case in which the reduction ratio is 1, and FIG. 26 shows a case in which the reduction ratio is larger than 1. The wire 51 is connected to the driven link 92 in the same manner as shown in FIGS. 1A and 1B and the like, and the wire 51 is doubled in the vicinity of the connection. The driving pulley 91 is fixed to the input rotation shaft 52 and rotates in association with rotation of the input rotation shaft 52. In addition, in the case where a clamping member is used for connection between the wire 51 and the driven link 92, the clamping member can be located toward the driving pulley 91 from the center as in the case shown in FIG. 17. Furthermore, a clamping member such as shown in FIG. 21 may be used for connection between the wire 51 and the driven link 92.

Since the pulley rotates over a wider range than the link, the rotation range of the driving part is less limited in the mechanisms shown in FIGS. 24 to 26 than in the mechanism shown in FIGS. 1A and 1B and the like.

Figure 27:
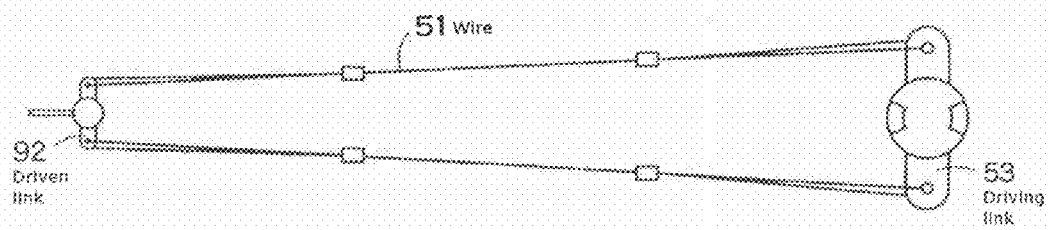
FIG. 27 is a diagram showing a case in which the reduction ratio is less than 1.
Figure 28:
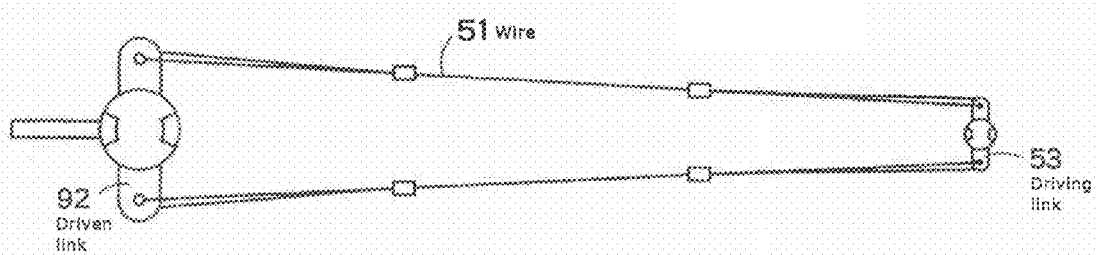
FIG. 28 is a diagram showing a case in which the reduction ratio is larger than 1.

FIGS. 27 and 28 are front views showing examples of a power transmission mechanism in which links are used both for the driving part and the driven part. FIG. 27 shows a case in which the reduction ratio is less than 1, and FIG. 28 shows a case in which the reduction ratio is larger than 1. In the cases shown in FIGS. 27 and 28, the wire 51 is doubled in the connections to the driving link 53 and the driven link 92, so that the wire 51 is more unlikely to break, and the safety and reliability are increased. In addition, since no pulley is used, the wire is not repeatedly subjected to a bending stress, and thus, the reliability of the wire 51 is further increased.

As described above, according to the second embodiment, a highly safe and reliable power transmission mechanism can be provided by arbitrarily combining the driving pulley 91 or the driving link 53 and the driven pulley 54 or the driven link 92 and appropriately determining the reduction ratio.

Third Embodiment

A third embodiment is applied to the driving link 53 that has the mechanical fuse mechanism shown in FIG. 15. According to the third embodiment, it is possible to easily externally detect whether the mechanical fuse is activated or not.

FIG. 29 includes diagrams showing structures of the input rotation shaft 52 and the driving link 53 according to the third embodiment. FIG. 29A is a front view of the input rotation shaft 52, FIG. 29C is a plan view of the input rotation shaft 52, and FIG. 29B is a front view of the driving link 53, and FIG. 29D is a plan view of the driving link 53.

Figure 29C:
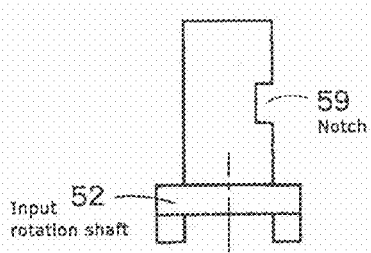
FIG. 29C is a plan view of the input rotation shaft 52.
Figure 29D:
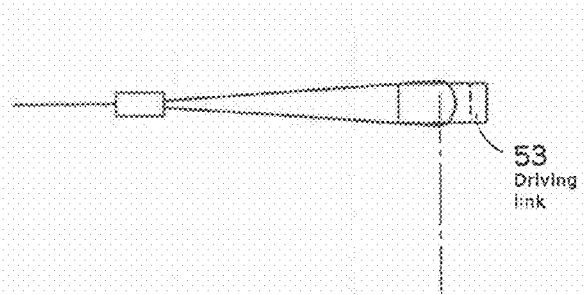
FIG. 29D is a plan view of the driving link 53.
Figure 29A:
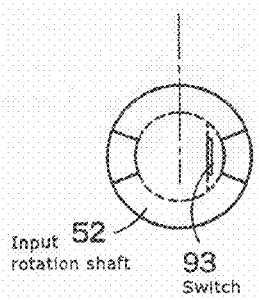
FIG. 29A is a front view of the input rotation shaft 52.
Figure 29B:
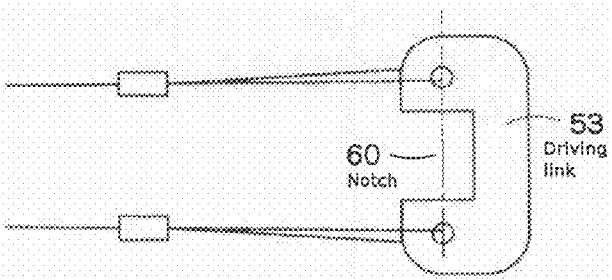
FIG. 29B is a front view of the driving link 53.
Figure 30C:
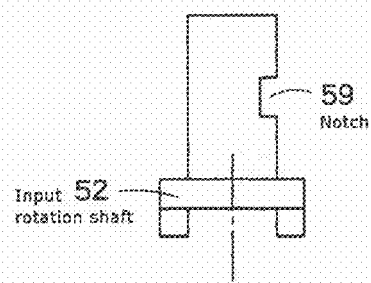
FIG. 30C is a plan view of the input rotation shaft 52.
Figure 30D:
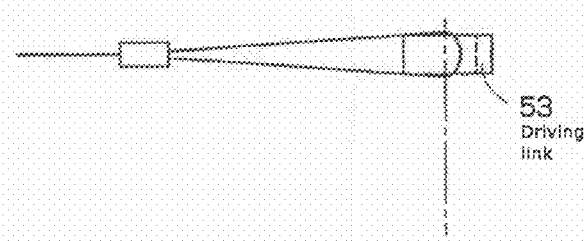
FIG. 30D is a plan view of the driving link 53.
Figure 30A:
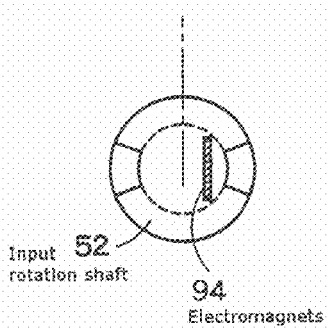
FIG. 30A is a front view of the input rotation shaft 52.
Figure 30B:
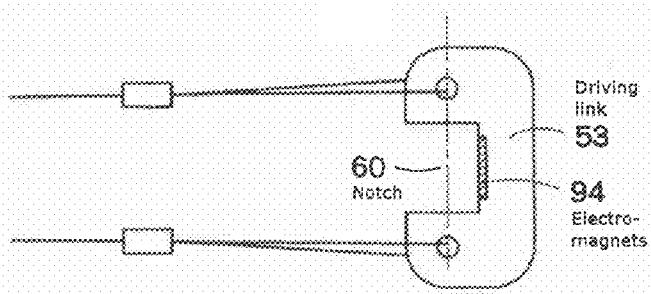
FIG. 30B is a front view of the driving link 53.
Figure 31C:
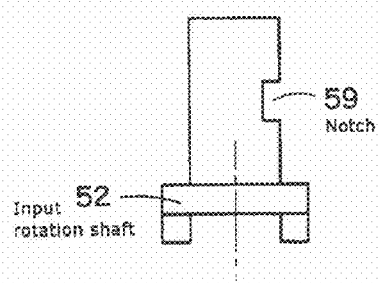
FIG. 31C is a plan view of the input rotation shaft 52.
Figure 31D:
FIG. 31D is a plan view of the driving link 53.
Figure 31A:
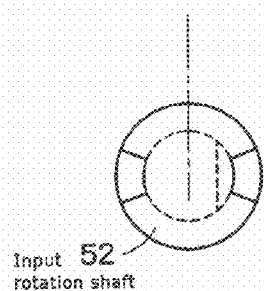
FIG. 31A is a front view of the input rotation shaft 52.
Figure 31B:
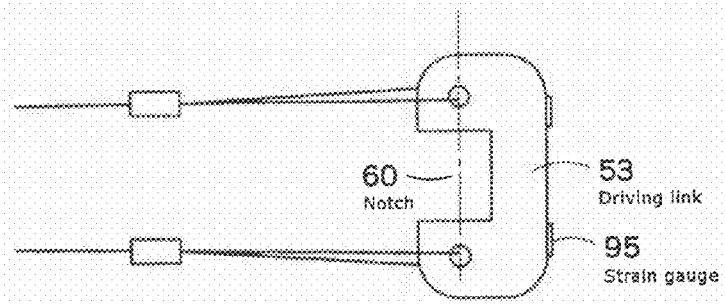
FIG. 31B is a front view of the driving link 53.

As shown in FIGS. 29A and 29C together, in the notch 59 of the input rotation shaft 52, a switch 93 for detecting a contact with the notch 60 of the driving link 53 is provided. The switch 93 is held in ON state when the switch is in contact with the notch 60 of the driving link 53, and held in OFF state when the switch is not in contact with the notch 60, that is, when the mechanical fuse is activated. A signal indicating the state of the switch 93 is sent to the control device 2 shown in FIG. 5. The control device 2 makes the monitor device 24 shown in FIG. 4 indicate ON/OFF state of the switch 93. Therefore, the operator can easily and quickly know whether the input rotation shaft 52 and the driving link 53 are normally engaged with each other or not.

The switch 93 may be disposed in the notch 60 of the driving link 53, but not in the notch 59 of the input rotation shaft 52. In addition, the type of the switch 93 is not limited to a particular one, and a wide variety of switches or sensors may be used, such as a mechanical contact switch and a pressure sensitive sensor.

As described above, according to the third embodiment, since the switch 93 is disposed at the engaged portion between the driving link 53 and the input rotation shaft 52, an abnormal engagement between the driving link 53 and the input rotation shaft 52 can be easily and quickly detected, and malfunctions can be prevented.

Fourth Embodiment

According to a fourth embodiment, the engagement between the driving link 53 and the input rotation shaft 52 is enhanced.

FIG. 30 includes diagrams showing structures of the input rotation shaft 52 and the driving link 53 according to the fourth embodiment. FIG. 30A is a front view of the input rotation shaft 52, and FIG. 30C is a plan view of the input rotation shaft 52. FIG. 30B is a front view of the driving link 53, and FIG. 30D is a plan view of the driving link 53.

Electromagnets 94 are disposed in the notch 59 of the input rotation shaft 52 and the notch 60 of the driving link 53 in such a manner that the electromagnets 94 face each other. The electromagnets 94 have opposite polarities, so that when the notches are positioned to face each other, the magnetic force acts to bring the notches close to each other, and the attraction between the input rotation shaft 52 and the driving link 53 increases.

Since the electromagnet 94 produces the magnetic force by means of a coil (not shown), the magnetic attraction can be eliminated by cutting off the current flowing to the coil. In this case, only the mechanical attraction remains. Furthermore, the magnetic attraction can be adjusted by changing the amount of the current flowing to the coil. Furthermore, by using electromagnets having the same polarity, a repulsive force can be produced, thereby further reducing the attraction. In addition, a desired adjustment range for the attraction can be achieved by using a stretch spring to the engaged portion so as to achieve a state having an attraction less than the mechanical attraction and by using a function for increasing the attraction by the electromagnet.

As described above, according to this embodiment, the attraction between the input rotation shaft 52 and the driving link 53 can be adjusted stepwise. For example, in the case of a medical manipulator that performs an operation that involves a high load imposed on the tip or a medical manipulator that performs an operation that requires a high holding force, the input rotation shaft 52 is frequently subjected to a high torque. Therefore, if the structure of the manipulator and the attraction between the engaged parts thereof are much the same as those of other manipulators that perform a low-load operation, the required specifications cannot be met. Although the attraction can be changed by changing the depths of the notches 59 and 60 as described above with regard to the first embodiment, it is impossible change the depths of the notches 59 and 60 each time the load changes. In addition, replacing one operator with another depending on the type of operation is burdensome. Thus, if the attraction between the input rotation shaft 52 and the driving link 53 can be electrically adjusted as in this embodiment, the attraction can be changed depending on the load, so that the operator can be used for a wide variety of applications.

Fifth Embodiment

According to a fifth embodiment, the tension of the wire 51 connecting the driving link 53 or driving pulley 91 and the driven link 92 or driven pulley 54 to each other is measured easily and accurately.

FIG. 31 includes diagrams showing structures of the input rotation shaft 52 and the driving link 53 according to the fifth embodiment. FIG. 31A is a front view of the input rotation shaft 52, and FIG. 31C is a plan view of the input rotation shaft 52. FIG. 31B is a front view of the driving link 53, and FIG. 31D is a plan view of the driving link 53.

While the input rotation shaft 52 has the same structure as in the first embodiment, the driving link 53 is provided with a strain gauge 95. The strain gauge 95 is attached to the upper, lower or side face of the driving link 53. If the wire 51 hung through the opening 55 of the driving link 53 comes off, the tension exerted on the driving link 53 rapidly decreases, so that the tension measured by the strain gauge 95 also considerably changes. Therefore, it is possible to recognize that the link is disengaged from the tension measured by the strain gauge 95. Thus, a failure, such as a break in the wire 51, can be readily and quickly detected, and a highly safe power transmission mechanism can be provided.

The strain gauge 95 may be attached directly to the wire 51, instead of being attached to the driving link 53. In this case, the tension of the wire 51 can be more quickly and accurately detected, and the torque of the motor (not shown) that drives the input rotation shaft 52 can be accurately estimated. For example, when the input rotation shaft 52 and the driving link 53 are engaged with each other, the motor torque changes within a certain range as the motor rotates. The motor torque can be measured by measuring the motor current. If the input rotation shaft 52 and the driving link 53 are disengaged from each other, the motor torque becomes lower than a prescribed value, and the motor current value falls outside a normal range. Therefore, by continuously monitoring the change of the motor current, the state of engagement between the input rotation shaft 52 and the driving link 53 can be accurately monitored.

In the case where the driving pulley 91 is used instead of the driving link 53, the strain gauge 95 can be attached to the driving pulley 91.

While the power transmission mechanism applied to the medical manipulator has been described above with regard to the first to fifth embodiments, the power transmission mechanism according to the present invention can be equally applied to various robots other than the medical manipulator.

What is claimed is:

1. A robot comprising:
   a flexible power transmission member;
   an input rotation axis rotated by a power generation source;
   a driving link connected at both ends of the flexible power transmission member, which transmits a rotation torque of the input rotation axis to the flexible power transmission member; and
   a driven pulley around which the flexible power transmission member is hung, wherein
   the input rotation axis has a first notch; and
   the driving link has a second notch capable of engaging with the first notch,
   engagement between the first notch and the second notch being released when an overload is exerted on at least one of the driving link or the driven pulley, and the first notch and the second notch being again engaged with each other when the overload is removed.

2. The robot according to claim 1,
   wherein a length of the driving link is longer than a diameter of the driven pulley.

3. The robot according to claim 1, further comprising:
   a clamping member which fixes the flexible power transmission member passing through an opening formed in the driving link between the driving link and the driven pulley,
   wherein the flexible power transmission member is hung through the driving link by passing through the opening; and
   the flexible power transmission member is doubly connected between the clamping member and the driving link, and is singularly connected between the clamping member and the driven pulley.

4. The robot according to claim 3,
   wherein the clamping member is arranged closer to the driven pulley than an intermediate position between the driving link and the driven pulley.

5. The robot according to claim 3, further comprising:
   a clamping member attached to the driving link, the clamping member fixing the flexible power transmission member to the driving link.

6. The robot according to claim 1, further comprising:
   a contact detector which detects an engagement state between the first notch and the second notch.

7. The robot according to claim 1, further comprising:
   an electromagnet which generates at least either of attraction or repulsion between the first notch and the second notch.

8. The robot according to claim 1, further comprising:
   a strain gauge attached to the driving link or the flexible power transmission member, which measures a tension exerted to the flexible power transmission member.

9. The robot according to claim 1, wherein the second notch is deeper than the first notch.

* * * * *